United States Patent [19]

Tamari

[11] Patent Number: 5,429,483
[45] Date of Patent: Jul. 4, 1995

[54] PRESSURE SENSITIVE VALVES FOR EXTRACORPOREAL PUMPING

[76] Inventor: Yehuda Tamari, 21 Singworth St., Oyster Bay, N.Y. 11771-3703

[21] Appl. No.: 16,034

[22] Filed: Feb. 10, 1993

Related U.S. Application Data

[63] Continuation-in-part of Ser. No. 852,931, Mar. 13, 1992, Pat. No. 5,186,431, which is a continuation of Ser. No. 683,093, Apr. 10, 1992, abandoned, which is a continuation of Ser. No. 410,845, Sep. 2, 1989, abandoned.

[51] Int. Cl.⁶ .............................. F04B 43/08
[52] U.S. Cl. ........................... 417/307; 417/474
[58] Field of Search ............ 417/307, 474–479, 417/477 R; 604/9, 153, 154

[56] References Cited

U.S. PATENT DOCUMENTS

| | | | |
|---|---|---|---|
| 4,515,536 | 5/1985 | van Os | 417/474 |
| 4,515,589 | 5/1985 | Austin et al. | 417/477 |
| 4,552,552 | 11/1985 | Polaschegg et al. | 604/9 |
| 4,650,471 | 3/1987 | Tamari | 417/474 |
| 5,052,900 | 10/1991 | Austin | 417/477 R |
| 5,215,450 | 6/1993 | Tamari | 417/474 |
| 5,222,980 | 6/1993 | Gealow | 417/474 |
| 5,273,406 | 12/1993 | Feygin | 417/474 |
| 5,336,051 | 8/1994 | Tamari | 417/474 |

FOREIGN PATENT DOCUMENTS

| | | | |
|---|---|---|---|
| 1216427 | 3/1986 | U.S.S.R. | 417/477 R |
| 1229425 | 5/1986 | U.S.S.R. | 417/477 R |

Primary Examiner—Richard A. Bertsch
Assistant Examiner—Peter Korytnyk
Attorney, Agent, or Firm—Scully, Scott, Murphy & Presser

[57] ABSTRACT

The specification describes several uses for pressure sensitive valves during extracorporeal pumping in one embodiment, an improved pumping loop for a roller pump is used in an extracorporeal circuit with a pressure relief valve and pump tubing. The inlet and outlet of the tubing are connected respectively to the outlet and inlet of said valve via two 3 way connections, across the outlet of the pump. The pumping loop allows recirculation of pumped liquid between the inlet and outlet of the pump when the outlet pressure generated by said pump exceeds a set value thereby limiting the pump outlet pressure to the set pressure. The pressure relief valve can also be placed at the inlet if the pump to protect the circuit from excess negative pressure that the pump can generate. The pressure relief valve in combination with the pump loop provides an accurate means to dynamically set the occlusion of the tubing within the roller pump.

29 Claims, 9 Drawing Sheets

PRESSURE SENSITIVE VALVES FOR EXTRACORPOREAL PUMPING

CROSS-REFERENCE TO RELATED APPLICATIONS

This application is a continuation in part of allowed application U.S. Ser. No. 07/852,931 filed Mar. 13, 1992, now U.S. Pat. No. 5,186,431, which was a continuation of U.S. Ser. No. 07/683,093 filed Apr. 10, 1992, now abandoned, which was a continuation of U.S. Ser. No. 07/410,845 filed Sep. 2, 1989, now abandoned, all of which were entitled "Pressure Sensitive Valves For Extracorporeal Circuits", allowed application U.S. Ser. No. 07/669,641 filed Mar. 14, 1991 entitled "Innovative Pumping System For peristaltic Pumps"; and U.S. Ser. No. 876,627 filed May 6, 1992 entitled "A Compact Low Cost Pressure Regulating System" which contain similar pressure sensors and control systems, the disclosures of these applications being incorporated herein by reference thereto.

BACKGROUND OF THE INVENTION

The simplicity and availability of the standard roller pump have made it the pump of choice for extracorporeal circulation. This pump is widely used in dialysis, routine cardiopulmonary bypass and long term pumping such as extracorporeal membrane oxygenators, (ECMO) and left and/or right heart bypass. The standard roller pump maintains a constant flow independent of clinically expected changes in inlet or outlet pressures. Thus, a decrease in blood supply at the pump inlet, without a concomitant decrease in pump speed, can cause excessive suction leading to air embolism, thrombosis and damage by the "venous" cannula to the vessel's intima. The combination of constant flow and an arterial line that is accidentally clamped or kinked, or an arterial cannula that is positioned against the vessel intima, can generate excessive pressures at the outlet of the pump which at the extreme, can blow up a connector, tube or an oxygenator.

To overcome these potential dangers in closed systems such as ECMO or dialysis, collapsible bladders have been placed at the inlet to the pump such that at too high a suction, the bladder collapses actuating a microswitch which stops the pump. The pump restarts when the bladder refills. Others have designed roller pumps with a servomotor and a microprocessor control system. When the roller pump is used during cardiac surgery for venting the left ventricle or for returning shed blood from the chest cavity it requires constant surveillance by a trained perfusionist to assure that no excess suction is applied.

Presently protection against extreme inlet or outlet pressures that may be generated by the roller pump require either on-off control with the standard roller pump, extensive and expensive modifications to the standard pump (e.g., CAPS Stockert-Sorin, Sorin Inc. Irvine, Calif. 92714) or a watchful perfusionist. These techniques require invasive pressure measurement which has the disadvantage of requiring a sterile transducer and promoting stagnating blood in the pressure monitoring line that can lead to thrombosis. A heparin coating that inhibits thrombosis to the inner walls of the extracorporeal circuit cannot be applied to the open port used to measure pressure. U.S. Pat. Nos. 4,515,589 and 4,767,289 (manufactured by Sarns/3M Corp. as the "Safety Loop"), and 4,650,471, describe devices to be used with the roller pump that prevent too much suction. The former provides no adjustment over the pressure about which flow is controlled. The '471 patent describes adjustment capabilities for the inlet, but neither provides relief for overpressurization at the outlet of the pump. Another solution is to use a centrifugal pump such as that made by Biomedicus of Minneapolis Minn. Its flow characteristics permit a limited negative pressure and outlet pressure to be generated, its costs however are high, about $10,000 for the pump module and $200 for each of the disposable pump heads. It also can generate a negative pressure of 600 mmHg and an outlet pressure of over 800 mmHg, both of which valves exceed clinical usefulness and can be traumatic.

Hemolysis by roller pumps is due to crushing of blood cells between the walls of the tubing being squeezed and/or high shear rates possible with retrograde flow through nonocclusive tubing. Pump occlusion is set by measuring the drop rate of a column of liquid at the outlet of a stopped pump. Drop rates anywhere from 1 to 40 cm/min per 100 cm pressure difference are reported in the literature. The drop method has five major disadvantages: inaccuracy because of relatively large variation in tubing wall thickness (+/−0.003″), unequal extension of the two rollers, off center roller rotation, pump raceways that are not truly circular and, during fast drop rates, the pressure decreases as the liquid falls. Thus, proper occlusion setting requires averaging of multiple readings which is a time consuming effort. Although it is reported by Bernstein and Gleason (Factors influencing hemolysis with roller pumps, Surgery, 61:432–442, 1967) and Noon et.al. (Reduction of blood trauma in roller pumps for long-term perfusion, World J. Surgery 9:65–71, 1985) that hemolysis increases as the occlusion is increased, for very nonocclusive settings the drop rate is too fast to measure accurately. Others have suggested that roller occlusion be set by measuring a pressure drop at the outlet of the pump. With this method, the pump outlet is clamped, the pump is rotated to increase the pressure to the desired level, the pump is then stopped, and the rate of pressure drop measured. Occlusion setting by this method is very dependent on the compliance between the pressure transducer and the roller occluding the tubing: the larger the compliance the lower the occlusion. Both aforementioned methods use a stationary pump, referred to hereafter s static tests which rely on a measurement taken from a single point along the pump raceway and from a single roller to determine occlusion. It may be that one of the reasons that users generally do not set the pumps in a less occlusive manner, is the difficulty in doing so accurately. It would be of great clinical advantage to be able to provide control over the maximum pressure in an extracorporeal circuit and the maximum suction the patient is exposed to, as well as to provide a simple means to enable the user to set the pump nonocclusively and provide a standard roller pump with the advantages of a centrifugal pump without its associated high costs. These can be done with pressure sensitive valves and appropriate control devices.

In the medical field, valves known as Starling resistors, are made of a thin walled sleeve and require negligible transwall pressure difference to close them. They have been suggested for use to maintain or adjust pressure, (Robert Rushmore: Control of Cardiac Output, in Physiology and Biophysics 19th edition Ruch TC and Patton HD editors, WB Saunders Co. Phil. 1965).

These valves made of a sleeve sealed in a housing with means to pressurize the interluminal space (the space between the housing and the sleeve). Pressure applied to the interluminal space acts upon the wall of the sleeve forcing the opposite walls of the sleeve to meet and close shut. This external force on the wall is counteracted by the pressure within the lumen of the sleeve which tends to keep the walls apart. It is the net force of these two vectors that determines whether the sleeve is opened, closed or in between.

In industry, these valves are used as ON/OFF valves or as adjustable resistors known as pinch valves. Pinch valves are also used to adjust the resistance to flow using an external roller that pinches and thus controlling the degree of closure of the sleeve. If the wall of the sleeve is made sufficiently thin, the valve can also be used to transfer the pressure of the fluid within the sleeve to the interluminal space without significant changes in the transduced pressure. Thus, these devices can transmit the pressure of a fluid that may be corrosive to a pressure gauge while isolating the pressure gauge from the fluid.

U.S. Pat. No. 4,767,289 teaches that a Starling valve may be made of a thin wall tubing, both ends of which are sealed to a rigid connector which in turn are sealed to the housing providing flow through chamber. U.S. Pat. No. 4,515,589 teaches that the walls of the thin wall tubing may extend beyond the housing, be folded upon themselves and sealed over the external wall of the housing. Another manufacturing technique suggests that the inner wall of a resilient sleeve be affixed to the outer wall of the thin walled tubing and the outer wall of that sleeve be affixed to the housing. These techniques have one or more of the following disadvantages: 1) the thin wall tube is stressed over the edges of the housing, 2) the assembly requires sealing the thin wall tube to the connectors, 3) the discontinuities of the valve at the connection sight between the thin wall and the thick wall tubing can create turbulence and trapped vortices, a leading cause of thrombus generation, 4) the assembly is labor intensive and require multiple parts and 5) control over the interluminal pressure with present systems is provided by a cumbersome and bulky combination requiring a compliance chamber, a pressure manometer and interconnecting tubing.

These disadvantages may be the reasons for the lack of pressure sensitive valve available for clinical use. U.S. Pat. No. 4,250,872 by Tamari illustrates a valve made of unitary tubing a portion of which has been expanded and thinned walled to allow easy contraction by external fluid pressure. This valve however was not made to fully close (as illustrated in FIG. 5) nor was it preformed to close completely shut. The only pressure sensitive valve that is known to be used clinically in the extracorporeal circuit is the one incorporated at the inlet to the "Safety Loop" mentioned above. Its assembly is labor intensive and requires multiple parts. In addition, its housing is exposed to atmosphere and provides no mechanism to adjust the interluminal pressure. Senko Medical Instrument Mfg. Co., LTD. of Tokyo Japan manufactures a pressure relief valve intended for dialysis. It is made by interposing a thin wall a diaphragm made of a plastic sheet between the wall with the pressure port and the blood path. This method though very adaptable to mass production, results in a diaphragm that often is accidentally heat-sealed to the housing wall, preventing its free motion, thereby rendering it nonfunctional. It also has discontinuities at the connection sight between the thin wall and the thick wall tubing creating the areas of stagnation which are prone to thrombus formation.

The present invention discloses the use of elastic sleeves to set the pressure characteristics of a Pressure Relief Valve. Inflatable elastomeric bladders have been used for pressure indication and regulation (e.g., part no. BSVD-300, Shiley, Laboratories, Irvine, Calif., and U.S. Pat. No. 3,993,069). The pressure-volume characteristics of these balloons have a high or low frequency hysteresis, and/or the highest pressure occurs upon initiation of inflation and thereafter it decreases (e.g., see FIG. 1 of U.S. Pat. No. 3,993,069 and FIG. 6 of Tamari's U.S. Pat. No. 5,013,303). The Shiley device is a spherical balloon and therefore upon inflation its size, but not its shape, changes. Neither of these devices allow the user to adjust the pressure. It would be useful to have a pressure regulator with a shape change which indicates pressurization more clearly. It would also be of great advantage to provide the user with the means to adjust the maximum outlet pressure of pumps and incorporate inexpensive means to measure noninvasively the pressure of the pumped fluid.

SUMMARY OF THE INVENTION

The present invention provides the combination of a pressure relief valve (pressure relief valve) and an extra corporeal circuit to control pressure therein. In one embodiment, the pressure sensitive valve and pump tubing are interconnected via 3-way connectors, with the tubing placed in a peristaltic pump used for extracorporeal circulation and with said valve being normally closed. When outlet pressure generated by said pump exceeds a set value, the pressure relief valve opens allowing recirculation of pumped liquid between the inlet and outlet of said pump and thus preventing overpressurization. In another combination, a pressure sensitive valve that is normally open is placed at the inlet to the roller pump and is used to limit the negative pressure applied to said extracorporeal circuit. The pressure relief valve can also be used to accurately set the occlusion of said peristaltic pumps as well as to measure blood pressure noninvasively.

The pressure relief valve is preferably made of a single, indefinite length of uniform, smooth, fissureless, thermoplastic, elastomeric tubing which is flexible and clear, a section of which has been processed and sealed in a housing to form an interluminal chamber with means for adjusting pressure. The pressure between the sealed section of the tube and the housing (interluminal pressure) is adjusted via a port forming a communication with said interluminal chamber. The geometry of the processed section, in general having a thinner wall than the unprocessed tube, reduces the pressure difference across the wall required to move said wall. Thus, when the interluminal pressure is greater than the pressure inside the processed section the valve is closed, and vice-versa. When the pressure relief valve is placed between the inlet and outlet of a pump, the user can adjust the maximum outlet pressure of the pump by adjusting the pressure applied to the interluminal chamber. When the pump outlet pressure reaches the set pressure, the pressure relief valve opens, allowing excess pressure to be relieved by recirculating some of the flow. The interluminal pressure can, for example, be controlled by an elastic balloon as described in applicants U.S. Pat. No. 5,013,303, or by other mechanisms to be described herein. The processed section can also transmit pressure to the sealed interluminal space, allowing noninvasive pressure measurement.

The objective of the present invention is to incorporate into a single device, a means to limit excess pressure within an extracorporeal circuit and a means to simply and accurately set pump occlusion.

A further objective of the present invention is to provide a pumping loop, consisting of roller pump tubing whose inlet and outlet are interconnected via a pressure relief valve that limits excess pressure within an extracorporeal circuit and allows setting of pump occlusion simply and accurately, that will reduce hemolysis.

A further objective of the present invention is a tubing used with pumps that incorporates within its continuous length a modified section that allows noninvasive pressure measurement that is more accurate than that possible with unmodified tubing.

A further objective of the present invention is to provide a new overall system that provides the standard roller pump with the advantages of the centrifugal pump at a significant reduction in cost, as well as the added advantage of enabling the user to adjust the maximum outlet pressure with a simple compact pressure control device.

A further objective of the present invention is to provide a pressure relief valve with improved visual indication of its pressurized and its open or closed state.

Another objective of the present invention is to provide a fissureless continuous length of flexible, blood compatible, polymeric tubing with a smooth inner surface throughout that is used in extracorporeal circuits which incorporates a pressure relief valve to promote the ease of heparin coating and improve blood compatibility.

A further objective of the present invention is to modify, improve and provide a flow through an inline isolator between the blood and pressure monitors and/or other devices that require blood pressure (negative or positive) to function and/or control without contaminating the blood.

A further objective of the present invention is to form an extracorporeal circulation regulating valve wherein it replaces standard shunts that are presently clamped, e.g., arterio-venous or arterial filter shunt.

A further objective of the present invention is to make the devices disposable, atraumatic, biocompatible, long lasting, with predictable and clinically useful pressure-flow characteristics.

Other objectives, features and advantages of the present invention will become apparent by reference to the following detailed description of the presently preferred, but nonetheless illustrative, embodiments thereof with reference to the accompanying drawings wherein:

BRIEF DESCRIPTION OF THE DRAWINGS

FIG. 11b is an enlarged view illustrating a detail of a section of the pressure relief valve shown in FIG. 11a;

FIG. 17b illustrates a cross sectional view along line 17—17' of the pressure relief valve shown in FIG. 17a;

FIG. 18b illustrates a cross sectional view along line 18—18' of the pressure relief valve shown in FIG. 18a;

FIG. 20b illustrates a side view of the pressure relief valve and adjustable spring loaded clamp shown in FIG. 20a;

DETAILED DESCRIPTION OF THE PREFERRED EMBODIMENTS

Figure 1:
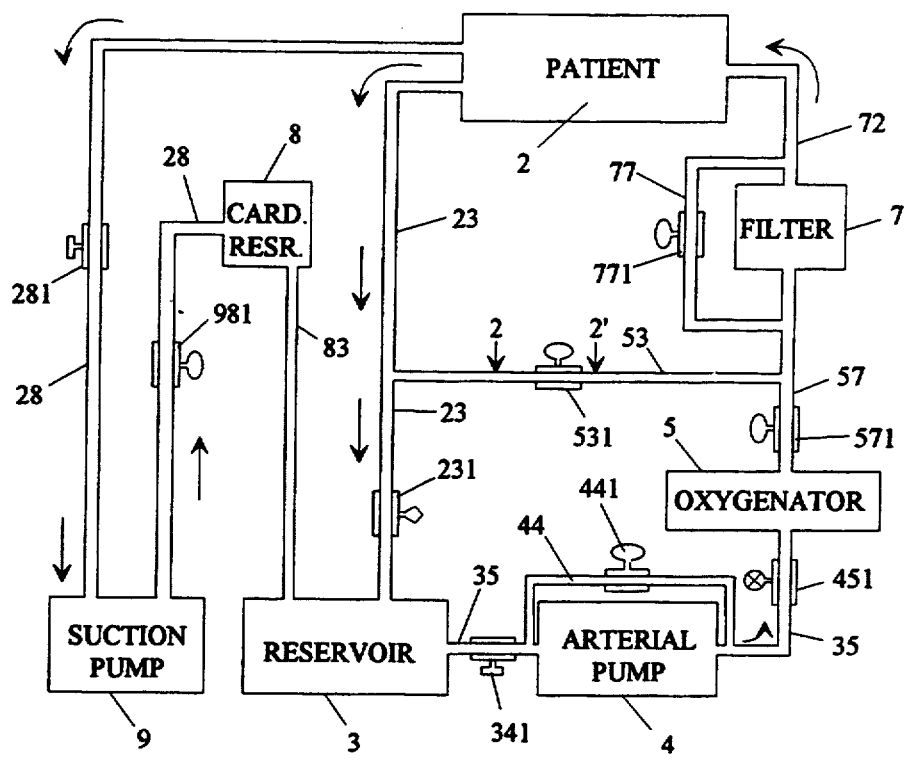
FIG. 1 is a schematic representation of a system according to the present invention and showing particularly pressure sensitive valves in various locations of a clinical cardiopulmonary bypass circuit, each valve with an associated pressure control device for controlling the valve according to its respective function.

Reference should now be made to the drawings wherein the same last two digits of the reference numerals are used throughout to designate the same or similar parts. It should be noted that the use of cardiopulmonary bypass, as shown in FIG. 1, is for descriptive purposes, and should not be taken as a limitation to the use of the devices described thereafter.

A typical extracorporeal circuit to which pressure sensitive valves in accordance with the present invention may be applied is illustrated in FIG. 1 as including a section of tubing 23 inserted at one end by means of a cannula (not shown) in the vena cavae for obtaining venous blood from the heart (not shown) of patient 2. Tubing 23 is coupled, as an example, to a venous reservoir 3. The blood is drawn from the venous reservoir 3 via tube 35 by roller pump 4 and pumped through a membrane oxygenator 5 wherein oxygen is supplied to the blood and carbon dioxide removed. The blood from the oxygenator is then conducted by means of tubing 57 to arterial filter 7 and then via tubing 72 and an arterial cannula (not shown) back to the patient. Blood spilling into the chest cavity (not shown) is collected via unitary tubing 28 by suction generated by roller pump 9 and pumped into cardiotomy reservoir 8 from which it flows by gravity drainage through unitary tubing 83 into venous reservoir 3. Pressure sensitive valves may be placed in various locations in the extracorporeal circuit depending on the desired purpose. Valves are shown as 281, 981, 231, 341, 441, 451, 531, 571 and 771 in FIG. 1.

A volume sensitive valve 231 is inserted between the patient and the inlet to venous reservoir 3 in unitary tubing 23. As will be hereinafter explained in detail, by adjusting the interluminal volume or pressure of valve 231, it is possible to vary the resistance to modulate the flow thereby controlling the venous blood flow to the venous reservoir. The interluminal volume can be adjusted by adding or removing volume with compressible or incompressible fluid. The use of incompressible fluid provides more accurate control over the absolute opening of the valve. Utilizing sterile physiological solutions, as for example saline, as the incompressible solution also provides a safety feature: should the thin wall section develop a leak, the blood would not be contaminated nor would it be exposed to a gas that could cause gas embolus.

Figure 22:
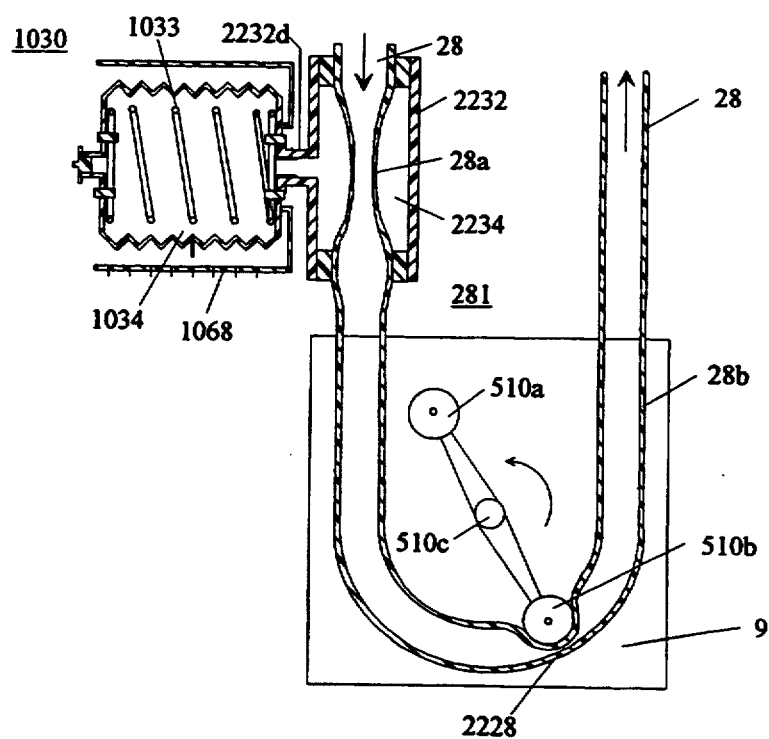
FIG. 22 shows one combination of a pressure relief valve that is normally open and a roller pump used for suction, wherein the pressure relief valve is used to limit suction applied to patient and/or set occlusion of said pump.

A pressure sensitive valve 341, inserted between reservoir 3 and the inlet to roller pump 4 in unitary tubing 35, protects against pumping air to the patient should the reservoir empty and may also be used to limit the maximum negative pressure applied to the blood as described in reference to FIG. 22. As will be hereinafter explained in detail, this is achieved by having the valve collapse to a closed state when the blood pressure decreases below a preset value usually equal to hydraulic pressure exerted by the minimum acceptable blood level of venous reservoir 3. Valve 341 reopens when the blood pressure reaches a value greater than the preset value of the valve. It should be noted that a volume sensitive valve is similar to a pressure sensitive valve except that the wall of the former may be thicker.

In the circuit shown in FIG. 1, it is necessary to prevent the entry of air into the blood stream through the micropores of a membrane oxygenator 5 if the gas pressure is greater than the blood pressure. This can occur when the membrane oxygenator is above the venous reservoir 3 or the gas outlet port is obstructed. To prevent the former, presently the venous reservoir 3 must be positioned above the membrane oxygenator, thus limiting venous drainage. An additional 20 to 30% increase in venous drainage could be provided if the reservoir could be placed below the membrane oxygenator. This can be achieved by placing prepressurized pressure relief valves 451, 571 at the inlet and outlet of the membrane oxygenators. Pressure sensitive valve 451 as described hereinafter, is incorporated in unitary tubing 35 between pump 4 and the inlet to oxygenator 5. Pressure sensitive valve 571 is incorporated into unitary tubing 57 at the outlet of oxygenator 5. The valves open when the inlet blood pressure is greater than the hydraulic height between the reservoir and the oxygenator. Thus, the two valves isolate the microporous oxygenator from the venous reservoir and assure that the pressure on the blood side of the microporous oxygenator is always above atmospheric pressure on the gas side. This has the advantage of being able to place the venous reservoir below the membrane oxygenator thereby providing greater gravity drainage presently not possible with known prior art devices. A pressure isolation feature of valve 451 also provides means to measure arterial line pressure without direct blood contact.

A pressure sensitive valve 531, acting as a pressure relief valve, is incorporated into unitary tubing 53 between the inlet and outlet of arterial pump 4, shown connected at oxygenator outlet tube 57 and venous line 23, prevents accidental overpressurization at the outlet of pump 4. The use of this valve provides additional clinical advantages not possible with the standard roller pump. For example, at the end of the operation when the patient is off cardiopulmonary bypass (CPB), blood is administered to the patient by pumping from the oxygenator through the arterial cannula. The surgeon tells the perfusionist to infuse 100 ml, the perfusionist unclamps the arterial line, turns the pump till 100 ml are infused and then shuts the pump off and reclamps the arterial line. This procedure requires coordination with the surgeon depending on the perfusionist for accuracy. With pressure relief valve 531, as the shunt between the arterial and venous line, the roller pump can be left on continuously and the surgeon can control blood administration directly by opening and closing a tubing clamp himself. Another advantage is, that in the event arterial filter 7 plugs up, valve 531 would open to prevent over pressurization of the arterial line and in addition would divert the blood from the patient back to the venous line. This is especially useful if the build up in pressure is due to thrombus, a clamped filter outlet, or an obstructed arterial cannula. It should be noted that should valve 531 open during CPB the blood volume at the inlet to the pump will tend to increase. This increase would be unlimited with an "open system" (e.g., bubble oxygenator) but would be limited to the capacity of the inlet reservoir (e.g., venous reservoir of membrane oxygenator). This implies that the use of a recirculating valve will benefit from a means to indicate that the valve is open. Reduction in flow to the patient can be indicated by reduction in the arterial pressure of the patient, a flow meter attached to the arterial line between valve 531 and the patient, or an alarm to indicate whenever the valve opens, as described hereinafter.

A pressure sensitive valve 441, incorporated into unitary tubing 44 and placed directly between the outlet and inlet of arterial pump 4 to form a pumping loop as shown in FIGS. 5a–5d, functions in an identical manner as valve 531 but its location provides additional protection against excess pressurization for devices between pump 4 outlet and recirculation line 53 containing valve 531. Either valve 441 or valve 531 can be used to set the occlusion of arterial pump 4 as explained with respect to FIGS. 5 and 7.

A pressure sensitive valve 771 can also be incorporated across the inlet and outlet of the arterial filter in unitary tubing 77 to prevent over pressurization of the arterial line due to a plugged filter.

A pressure sensitive valve 281, incorporated between the patient's chest cavity or a vented heart chamber and the inlet to suction pump 9, acts as a suction control valve and protects the patient 2 from excess negative pressure. This valve stays open as long as the blood pressure between the pump and the patient is higher than that set by the user or manufacturer. Valve 281 can also be used to set the occlusion of suction pump 9 as explained with respect to FIG. 22.

A pressure sensitive valve 981 may be incorporated into unitary tubing 28, between roller pump 9 and the inlet to cardiotomy reservoir 8, and opens only if the blood pressure is above the interluminal pressure. If the interluminal pressure is maintained slightly positive, and the cardiotomy reservoir 8 is open to atmosphere, then if suction pump 9, when used for venting one of the heart chambers, is accidentally reversed, valve 981 would close, preventing pumping air back to the patient.

As described, the pressure sensitive valves of the present invention can be used to: open and relieve excess pressure, close when the pressure drops too low, adjust resistance to flow and transmit a pressure signal across its wall. Each application may require a slightly different means for setting the predetermined pressure, the basic valve construction can remain the same. The specific operation, related design and different applications of each valve is hereinafter described.

Figure 2:
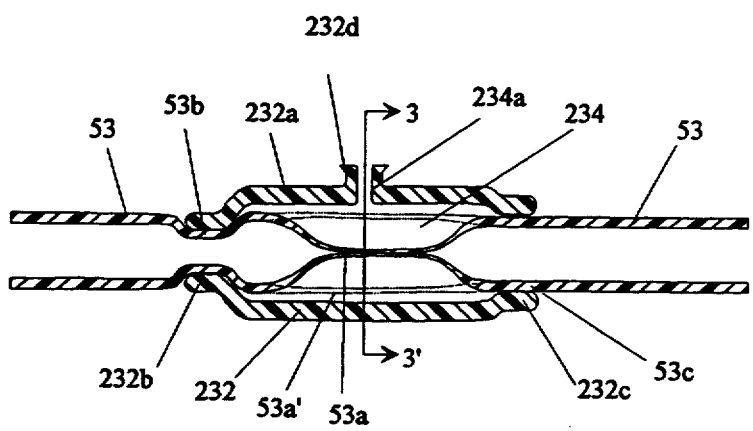
FIG. 2 is a sectional view of valve 531 taken between lines 2 and 2' in FIG. 1 illustrating one preferred embodiment of a pressure sensitive valve.
Figure 3:
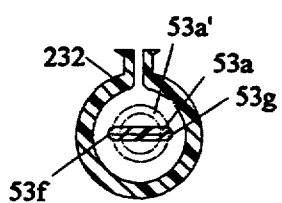
FIG. 3 is a transverse sectional view taken along lines 3 and 3' in FIG. 2 showing the expanded and contracted configuration of the inner thin wall tubing.
Figure 6:
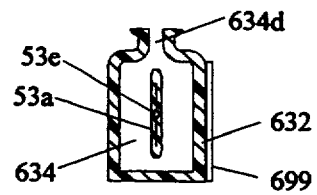
FIG. 6 is a transverse sectional view taken along lines similar to 3 and 3' in FIG. 2 showing a housing with improved optical characteristics and a pressure relief valve rotated 90°. The thin wall tubing therein has a single bleed channel.

FIG. 2 illustrates one presently preferred embodiment of the pressure sensitive valve which is illustrated in use in FIG. 1 as 231, 281, 341, 441, 451, 531, 571, 771, and 981. Valve 531 includes a unitary tubing member 53 passing through a generally cylindrical or elliptical housing or enclosure 232 which is nonelastic in construction using a clear thermoplastic material such as polycarbonate, polyvinylchloride, PETG or the like. Tubing member 53 preferably consists of a continuous length of blood compatible, flexible, polymeric, transparent material having a smooth fissureless inner surface throughout. It is useful for the material to be thermoplastic so as to allow the formation of the thin wall after the tube has been extruded. It may be formed from polyvinylchloride, polyurethane, C-Flex (Concept Polymer Technologies Inc., Clearwater, Fla. 33546) or the like. To reduce the pressure difference across the thin wall required to close the valve it is advantageous for the material of tube 53 to be relatively soft with a shore hardness in the range of 40A to 75A. For example, Tygon S-40-HL with a shore hardness of 40A or Tygon S-62-HL with a shore hardness of 55A both made by Norton Co of Akron Ohio are preferable choices. As illustrated, tube 53 has a region 53a intermediate its ends with a thinner wall than that of the remainder of the tube. The tubing has a gradual transition in wall thickness between the two said regions. The rigid walled enclosure 232 surrounds region 53a and seals it about regions 53b and 53c of said tubing. Inlet opening 232b and outlet opening 232c of housing 232 are snug fit to seal to the outside normal diameter of tubing member 53 on either side beyond the central region 53a. The midportion of housing 232 has an enlarged region 232a, at least in one aspect of its diameter as shown in FIG. 6, which accommodates the enlarged region 53a of unitary tubing 53 as it collapses to its closed state, as illustrated in FIG. 3. A duct 232d is joined to or formed at housing 232 and communicates with chamber 234, formed between the housing 232 and region 53a. Duct 232d is then connected to a pressure controller such as the pressure controller illustrated in FIG. 8. For the purpose of sealing seals 53b and 53c via radio frequency, heat sealing or adhesive, or solvent, or for other connective purposes it is advantageous, but not necessary, to form the housing 232 of the same material as the unitary tubing 53. Housing 232 may also be designed to serve as mechanical support for the thin section of region 53a to prevent accidental rupture due to over herniation of region 53a which could occur when the interluminal pressure is low and the blood pressure is high. Housing 232 may be blow molded for example from a clear material such as polycarbonate, polyvinyl chloride, PETG or the like with its walls somewhat inelastic but not necessarily rigid. It can also be vacuum formed as a clam shell with section 53a of unitary tubing 53 placed within both halves and then sealed by joining the halves to form the closed clam shell. Outlet region 53b can be, but does not have to be, constricted by 232b of housing 232 as shown, the purpose of which is described below.

Figure 4:
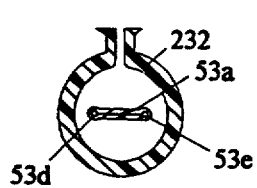
FIG. 4 is a transverse sectional view taken along lines 3 and 3' in FIG. 2 showing another preferred cross section of a pressure relief valve in a contracted state modified to form two bleed channels.

During operation of the pressure sensitive valve, pressurized fluid (or fluid mass) is introduced through duct 232d into chamber 234 whereupon the pressure causes indentation or contraction of the thin walled region 53a of said tubing to displace any blood contained therein leading to controlled restriction of the blood flow in unitary tubing 53 from the arterial line 57 to venous line 23. This restriction can be complete as illustrated in FIG. 3 or with small bleed channels as illustrated in FIG. 4 by 53d and 53e. To assure full closure of section 53a as illustrated in FIGS. 3, 4 and 6 at lower pressure differences between controlling interluminal pressure and blood pressure, edges 53g and 53f are preformed, for example with heat, to overcome the otherwise relatively high stresses inherent in the material that resist folding. It should be understood that for valves used to isolate (e.g., valve 571 isolating oxygenator 5 in FIG. 1) a complete obstruction to flow, as illustrated in FIG. 2, and 3, is required and the channels illustrated at 53a in FIGS. 4, and 6 are undesirable.

As long as the fluid pressure in first pressure chamber 234 acting externally on the thin wall tube 53a is greater than the pressure inside the tubing, the valve remains closed. If the pressure inside the tubing is greater than the external fluid pressure, the valve opens, as shown by the dashed lines in FIG. 3 which is a transverse sectional view taken along lines 3—3' in FIG. 2. If the pressure at the inlet to the valve is higher and the pressure at the outlet is lower than the external pressure then the valve does open but only partially and serves as a resistor that maintains inlet pressure at a pressure approximately equal to the fluid pressure applied in chamber 234. It should be understood that when the valve is used at the outlet of a constant flow pump (e.g., roller pump), the cross sectional area opened to flow decreases as the thin walled region of the valve collapses. The combination of decreased area and constant flow causes blood velocity and the blood pressure in region 53a to increase and decrease respectively according to Bernoulli's equation. The lower blood pressure in region 53a reduces the interluminal pressure at which the valve will close. If the resistance at the outlet of said pressure sensitive valve is low, as is the case between valve 531 outlet and venous reservoir 3, then the valve will flutter between opened and closed positions, the frequency of oscillation being higher with low viscosity (dilute blood) and high Reynold's number (higher flow rates). This property can be used to alarm the user to an open valve condition. For example, if the pressure sensitive valve is used as a pressure relief valve between the arterial and venous lines (531) or across the inlet and outlet of an arterial filter (771), then clinically it would be very useful to have an alarm incorporated into the valve design to alert the user to the dangerous condition. This can be done with the fluttering that occurs when the valve opens. For other uses, as for example the pressure sensitive valve acting as a resistor (231), or a continuous recirculating line, it is undesirable to have fluttering because over time it may cause blood damage. It therefore would be very useful to be able to control the degree of or eliminate fluttering.

One method of reducing flutter, according to the present invention, consists of placing a resistance between the port of the pressure relief valve and the pressure regulator. Said resistance could, for example, be the roller clamp valve type used with IV drip sets to adjust the rate of intravenous solution administration. Said resistance, in combination with a fluid of appropriate viscosity in interluminal space and the pressure regulator can be used to control the rate of volume change between the interluminal space and the pressure regulator and thus the rate at which the pressure relief valve can open or close. Increasing the resistance by closing the valve (or by increasing the viscosity of the fluid) reduces the flow rate between the interluminal chamber and the regulator thus providing increased damping that results in decreased fluttering. The resistance can also be controlled by inserting various lengths and/or diameters of tubing between the chamber and pressure regulator.

Figure 14:
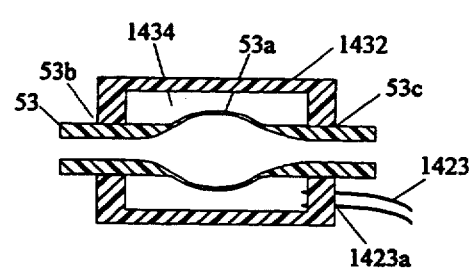
FIG. 14 illustrates an alternate embodiment forming a first pressure chamber for a pressure relief valve utilizing a thermoplastic cylindrical housing sleeve that is heat sealed to unitary tubing on each side of thin wall portion as well as to a pressure control line.

Another method that may reduce fluttering of region 53a illustrated in FIG. 2, is to increase the diameter of region 53a as illustrated in FIG. 14 so as to decrease the velocity of the blood therethrough and thereby reduce the pressure differences across the wall of region 53a that is due to differences in blood velocity in region 53a and the normal section of unitary tubing 53. Alternately, an equal or smaller ID in region 53a may increase the chance of flutter, a flow characteristic desirable for the aforementioned alarm.

Another method that may reduce fluttering is to increase the resistance at the valve outlet as for example decreasing the ID at the outlet of the valve as indicated by 53b in FIG. 2. The resistance at the pressure relief valve outlet can also be increased by using soft durometer wall tubing to make the valve. For example, if unitary tubing 53 has a durometer of 55A, (e.g., Tygon S-62-HL) the interluminal pressure is sufficient to compress the normal tubing wall. At typical operating conditions, with the controlling pressure being over 300 mmHg and the valve outlet pressure below 50 mmHg, the transwall pressure difference constricts the lumen of tube 53 whereby its cross section geometry resembles that shown in FIG. 4: with two channels that have a relatively higher resistance to flow than the naturally open lumen.

Another way to reduce flutter is to increase the wall thickness and or hardness of the thin wall section, 53a in FIG. 2.

To alarm the user to an open pressure relief valve, the pressure signal from its pressure port, 232d in FIG. 2, can be channeled to an arterial line pressure monitor with an alarm system (as made for example by DLP of Grand Rapids Mich.). Increased blood pressure would force the valve open, reducing interluminal space 234, thereby transmitting the increased pressure to the pressure monitor. Pressure transmission would be best achieved with a mixture of gas and liquid in chamber 234. The ratio of liquid to gas can be adjusted to provide sufficient compliance for the pressure relief valve to open without causing an undue increase in control pressure but sufficient for the pressure monitor to sense the increase.

Another advantage of the pressure relief valves described in FIGS. 2, and 11 through 16 is that they can transmit the intraluminal fluid pressure and thus can be used as devices to measure pressure noninvasively as described in my allowed applications U.S. Ser. No. 07/852,931 filed Mar. 13, 1992 entitled "Pressure Sensitive Valves for the Extracorporeal Circuit", and allowed U.S. Ser. No. 07/669,641 filed Mar. 14, 1991 entitled "Innovative Pumping System for Peristaltic Pumps", and two divisional applications filed Dec. 31, 1992 both entitled "Pressure Sensitive Valves for the Extracorporeal Circuit" which contain similar pressure sensors and control systems. It also would be obvious to those skilled in the art that such pressure sensitive valves could be used to control various functional parameters which require blood pressure control.

FIG. 4 illustrates housing 232 and thin wall tubing section 53a therein of valve 531, shown in FIG. 2, in a state of contraction with opposite walls flattened out to make contact and form a complete closure except for two bleed channels 53d and 53e formed at the edges of said tubing section. These channels allow sufficient blood flow through the tubing to hinder clot formation in tube 53 of valve 531 without taking away from its main purpose of causing an obstruction to flow. The flow through bleed channel 53d and 53e may be for example 1 to 5% of the pump flow. The channels may be formed naturally by the elastic properties of the material which dictate that the greatest stresses occur along the edges that fold. Or, if necessary, the channels may also be formed by heating the thin walled section and forming the channels with appropriate dies. The low flow provided by the leak can prevent stagnation of blood and thus reduce thrombus formation. To further reduce the occurrence of thrombus, it is advantageous to increase the blood velocity in tube 53. This can be achieved for example by making the diameter of unitary tube 53, shown in FIG. 1, equivalent to the diameter of the arterial cannula thereby limiting the additional pressure required at the pressure relief valve inlet when full pump flow is directed through it, to that seen under normal pumping conditions. In the preferred diameter the branch Y can be smaller to accommodate a pressure relief valve with smaller ID tubing. For example, pressure relief valve made of ¼" ID unitary tubing placed across a pump with ⅜" ID tubing in the raceway. For this set up, a ⅜"×⅜"×¼" Y connector would be used. Though two channels are shown, it should be understood that a similar function can be served by one or more channels.

Alternatively, unitary tubing 53 can be formed of a highly elastic material such as silicone rubber, in which section 53a is permanently formed in the closed position, for example as illustrated in FIGS. 2-4, or 6, said section then requiring a predetermined blood pressure above the pressure in the interluminal space 234 to open section 53a of the corresponding pressure relief valve.

The additional pressure can be fixed during manufacture by adjusting the thickness of section 53a and the degree of stress put in the material. It should be understood that when valve 531 is made with elastic section 53a, then the wall thickness of section 53a can be thicker than the normal wall of unitary tubing 53. It also should be understood that the pressure required to open section 53a could be sufficiently high whereby housing 232 serves to support said section and first pressure chamber 234 need not be pressurized.

Figures 5A, 5D:
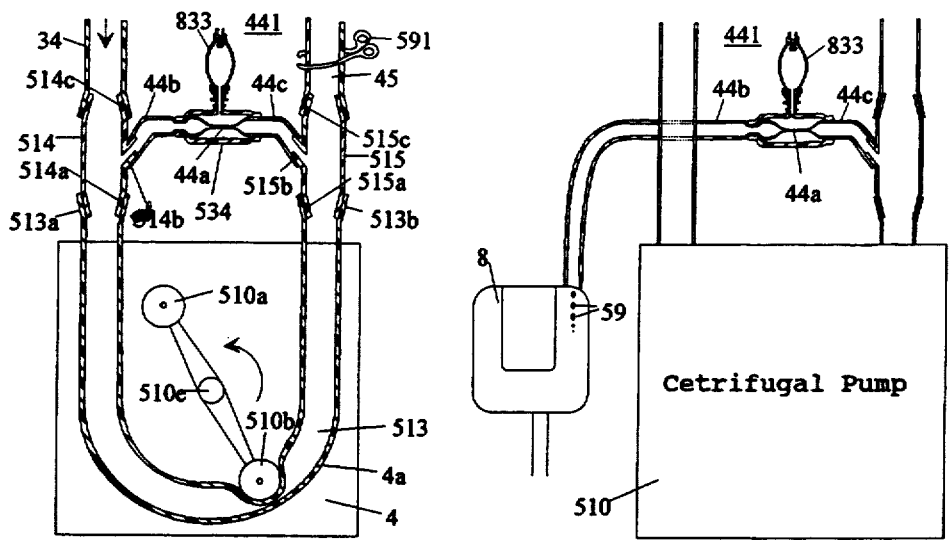
FIG. 5a is a schematic illustrating the combination of the pressure relief valve that is normally closed, the pump tubing as installed in a conventional roller pump, the 3-way connectors and their respective interconnection according to the present invention.
FIG. 5d is a schematic illustrating the combination of a pressure relief valve installed at the outlet of a centrifugal pump, a 3-way connector and a cardiotomy reservoir with their respective interconnection according to the present invention.

FIG. 5a is a schematic illustrating the combination of a normally closed pressure relief valve, the pump tubing, two 3-way connectors and their respective interconnection according to the present invention. As illustrated, pump tubing 513 is placed in roller pump 4 with its inlet 513a connected to 3-way perfusion connector 514 at 514a and its outlet 513b connected to 3-way perfusion connector 515 at 515a. Inlet tube section 44c of valve 441 is connected to port 515b of connector 515 and outlet port 44b of valve 441 is connected to port 514b of connector 514. Port 514c of connector 514 is connected to inlet tubing 34 and port 515c of connector 515 is connected to outlet tubing 45, said inlet and outlet tubing allowing the combination of pump 4, pressure relief valve 441, and pump tubing 513 to be incorporated within to a standard extracorporeal circuit. For example, inlet tube 34 can be connected to the arterial reservoir of a bubble oxygenator and outlet tube 45 can be the arterial line used to deliver blood to the patient during cardiopulmonary bypass. Another example would be for pump 4 to deliver blood cardioplegia with inlet tube 34 connected to the arterial reservoir of an oxygenator and outlet tube 45 connected to the heat exchanger. Similarly, pump 4 could be used in a dialysis circuit, with inlet tube 34 and outlet tube 45 incorporating said combination into said dialysis circuit as well known in the art of perfusion. As explained in detail for valve 531 in FIGS. 2-4, by adjusting the pressure of first pressure chamber of valve 441 it is possible to vary the blood pressure at which it would open, assuring that over pressurization anywhere in the circuit beyond the pump outlet would be prevented by allowing recirculation between pump outlet and inlet. The pressure of the first pressure chamber can be adjusted by adding or removing volume with compressible or incompressible fluid. The use of a sterile physiological solution, as for example saline, as the incompressible solution provides a safety feature: should the thin wall section develop a leak, the blood would not be contaminated nor would the possibility of gas emboli occur.

Pump 4, being a peristaltic pump, requires that its occlusion of tubing 513 be set appropriately. Occlusion by said pump of said tubing is set by adjusting the distance between rollers 510a and 510b, which extend radially, to squeeze tube 513 against pump raceway 4a. This can be achieved in the present invention by a dynamic method that gives an average occlusion over the entire segment of tubing 513 being used to pump blood. The method consists of pressurizing pressure relief valve 441 to a preset pressure, turning pump 4 on at a fixed rotation, clamping outlet tube 45, with for example tubing clamp 591 and adjusting the occlusion of pump 4, using occlusion setter 510e, until the recirculation flow through valve 441 is barely visible. This method, as will be described in reference to a visual indication with respect to FIG. 7, allows precise and accurate setting of various degrees of occlusions by simply adjusting the pressure of first pressure chamber of valve 441 and/or the pump speed at which flow through valve 441 just appears as shown in stage bb of FIGS. 7a and 7b.

When pump 4 is used to pump blood to a patient it would be useful for the user to know when overpressurization occurs and valve 441 opens. This can be accomplished by an alarm or by visual inspection of the valve and/or its outlet tubing (as will be described hereinafter). The reduction in flow to the patient that would accompany recirculation through valve 441 to the inlet of the pump can also be indicated by a reduction in the arterial pressure of the patient or comparing the reading from a flow meter attached to the arterial line between valve 441 and the patient to that expected for the pump speed being used.

Another method to determine the degree of recirculation through the valve is by clamping the tubing incorporating pressure relief valve 441 and noting the increase in either the pump outlet pressure or the patient arterial pressure. An increase that is greater than acceptable would suggest an unacceptably high recirculation rate.

The set up described in FIG. 5a can also be used to maintain a constant pump outlet pressure rather than constant flow as for example by setting the pressure of first pressure chamber 534 described in FIG. 2 to the desired pressure and allowing pump 4 to pump at a flow rate such that, without the pressure relief valve it would generate a pressure above that of the set pressure. In this setup, the valve would open allowing recirculation of excess flow through valve 4 maintaining the pump outlet pressure at the desired level.

Figures 5B, 5C:
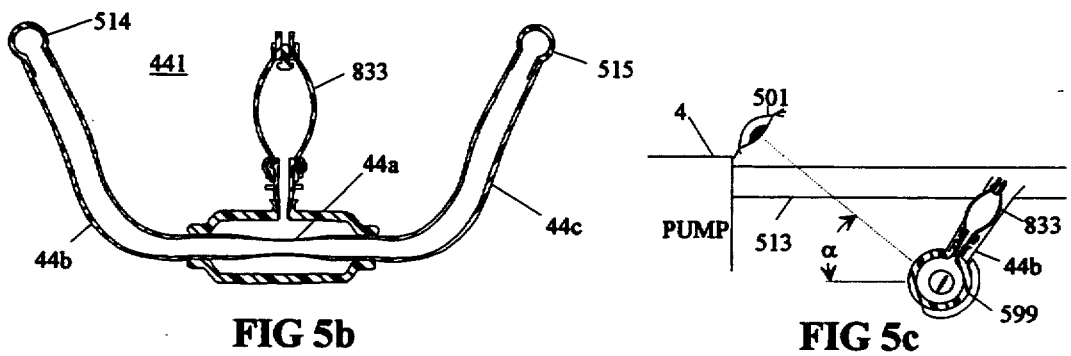
FIG. 5b is another view of the valve shown in FIG. 5a illustrating a transverse sectional view of one preferred relative orientation providing easier debubbling of said valve.
FIG. 5c is another view of the valve shown in FIG. 5a illustrating a transverse sectional view of one preferred relative orientation between the flattened portion of pressure relief valve and the pressure indicator that maximizes user view of valve open state and elastic sleeve pressurized state.

To avoid air entrapment within the recirculation line between ports 514b and 515b, it is advantageous to have sufficient length of tubing to allow valve 441 to be pushed below the horizontal plane of the said ports as illustrated in FIG. 5b. It is also useful to have said ports either point downward or to enable the user to push them downward when the circuit and pressure relief valve are primed and debubbled of air. This allows the lighter air to float to the top and be cleared from the pressure relief valve and its associated tubing.

FIG. 5b illustrates a transverse sectional view of one preferred relative orientation between the flattened portion of pressure relief valve and the pressure indicator that maximizes the user's view of the valve's open state and the elastic sleeve inflated (pressurized) state, as well as providing easier debubbling of said valve. The debubbling is enhanced by placing the valve below connector 514 and 515. This design feature provides the user with a clear view of any blood channeling as described in FIG. 7 below and the inflation state of the elastic balloon described in reference to FIG. 8. Debubbling is a standard operating procedure in which bubbles in the extracorporeal circuit are removed to prevent embolization of the patient.

FIG. 5c illustrates another sectional view of the pressure relief valve and pressure regulator combination shown in FIG. 5a, with a preferred permutation as defined by angle alpha, said angle being between 30° and 60° from the horizontal. Angle alpha allows an excellent visual angle between the user's eye 501 and said valve open state and said elastic sleeve inflated state.

FIG. 5d is a schematic similar to that shown in FIG. 5a except that the pressure relief valve 441 is shown with a centrifugal pump 510, and the outlet of valve 44b is connected to the top of a cardiotomy reservoir 8. As with the roller pump, the pressure relief valve prevents excess pressure at the pump outlet. Should outlet pressure exceed desired levels, the extracorporeal pressure will exceed the interluminal pressure, thereby opening thin wall section 44a. As the valve opens, it directs the pump flow associated with the excess pressure to the top of cardiotomy reservoir 8. If the connection from said valve to said reservoir is made at the top, as illustrated in FIG. 5b, an overpressure condition can be easily spotted by observing the flow at the air interface at the entrance to the blood reservoir 8 as shown for illustration only, by drops 59. Thus, the flow would indicate the degree of excess pressure in the extracorporeal circuit. If need be, the rate of flow through said valve could be measured by a timed collection of the volume accumulating in said reservoir whose outlet has been clamped shut.

Figures 7A, 7B:
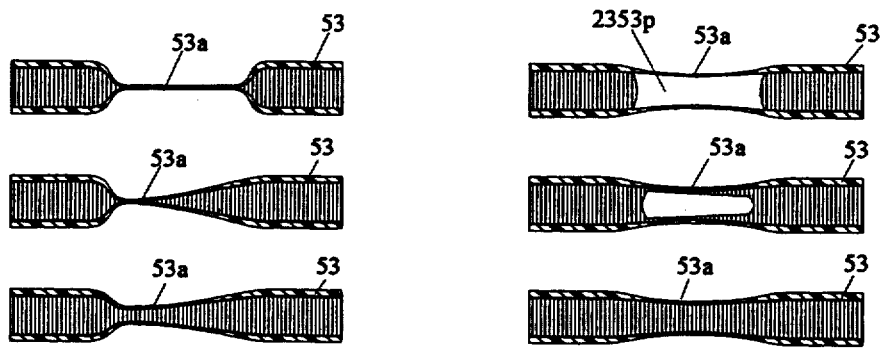
FIG. 7a illustrates the optical characteristics of a side view of a pressure relief valve in three stages: completely closed (aa), just opening (bb), and open (cc)
FIG. 7b is the top view of the pressure relief valve shown in FIG. 7a illustrating the optical characteristics of said valve when it is completely closed (aa), just opening (bb), and open (cc)

FIG. 6 illustrates another preferred embodiment of a pressure relief valve similar to that in FIG. 2 with an improved configuration to better visualize the open/closed state of thin wall region 53a, as described in reference to FIGS. 5 and 7. This is accomplished by forming housing 632 of rigid transparent material having a flat wall that is parallel to flattened wall of region 3a. When opposite walls of region 53a meet in a closed state they form a clear plane. When blood flows between these walls, the walls separate, said separation becoming visible due to lack of clarity and formation of at least one channel, (e.g., red streaks when the liquid is blood). FIG. 6 also illustrates a pressure relief valve with a single bleed channel, 53e, the purpose of which is to reduce thrombus formation. Also illustrated is the location of the pressure port for the pressure indicator/regulator, ideally it is either perpendicular as shown in FIGS. 2, 3 and 4, or parallel to the flattened plane of the thin wall section as shown in FIG. 6. The proper orientation of the port to the plane of the flat portion 53a depends on whether the degree of openness of the pressure relief valve is viewed as shown in FIG. 7a, where said perpendicular orientation is preferred, or as shown in FIG. 7b where said parallel orientation is preferred. Said proper orientation provides the user with a clear view of any blood channeling, as described in FIGS. 7a and 7b and the inflation state of the elastic balloon, hereinafter described with reference to FIG. 8, especially when the pressure relief valve is positioned as described in FIG. 5c.

FIG. 7a, also shown in a top view as FIG. 7b, illustrates how changes in optical characteristics in a pressure relief valve, as for example the one illustrated in FIG. 2, can be used to detect flow through it and/or its state of openness. When opposite walls of thin wall region 53a of a pressure relief valve, as for example that shown in FIG. 2 are squeezed close, they form a thin, clear flatten configuration as shown by plane 2353a in FIGS. 7a aa and 7b aa. When blood just starts to flow between these walls, the walls separate, said separation becoming visible due to an increase in thickness of said thin plane as well as due to a color change from clear to red through the entire length of the thin section 2353a as shown in FIGS. 7a bb and 7b bb. When the valve fully opens, said separation becomes more visible due to a further increase in thickness of said thin plane and increased area of said color change of the thin section 2353a as shown in FIGS. 7a cc and 7b cc. This unique feature can be used to dynamically set the occlusion of pump tubing 513 placed in roller pump 4 as shown in FIG. 5a. With this method, the occlusion is set by pressurizing pressure relief valve 441 to a preset value, clamping off outlet tube 45 with clamp 591, and adjusting the occlusion of pump 4 using adjuster 510e until, at a fixed rotation of pump 4, flow within valve 441 is barely visible, a visual state between FIG. 7a aa and 7a bb. For an under or over occlusive pump, the flow through the pressure relief valve would decrease or increase respectively as the pump occlusion is adjusted appropriately. To increase the optical differences shown in FIG. 7a between aa, bb and cc, it is desirable to have a white background to accentuate the said color change. This can be accomplished for example, with a white tape or white coloring placed on the housing wall opposite that being viewed, as shown for example by 699 in FIG. 6 and by 599 in FIG. 5c. The white coloring can also be impregnated within the material of the housing wall.

This dynamic method provides precise and accurate setting of various degrees of occlusions by simply adjusting the interluminal pressure of valve 441 and/or the pump speed at which flow through valve 441 occurs. Unlike the aforementioned static occlusion method, the dynamic method gives an average occlusion for both rollers over the entire segment of tubing 513 being used to pump the blood. It also measures directly the back flow such that a relationship between the speed of the roller pump and flow can be developed for any pressure difference between pump inlet and outlet (dP) and pump occlusion setting. Thus, at given occlusion setting, the net forward flow equals the total forward flow, which is the product of the pump speed and the pump constant, said constant being a function of the ID of pump tubing 513, less the back flow. The back flow, known from the occlusion setting (e.g., a flow equivalent to 5 RPM at a dP of 300 mmHg across said pump), can also be calibrated to produce a set of curves that give flow at any RPM and dP to give net forward flow. This concept was verified with an experiment where a ⅜" ID tubing was set non-occlusively using 5 RPM and dP of 300 mmHg as explained above and the flow of said tubing was compared to a tubing set occlusively. At a dP of 300 mmHg across the pump the flow of the nonocclusive pump was equal to that of the occlusive pump less a value equal to a flow of 5 RPM. Thus at 20 RPM the flow of the nonocclusive set pump was 450 ml/min as compared to 600 ml/min for the occlusive pump. Similarly, at 100 RPM, the flow of the nonocclusive set pump was 2850 ml/min as compared to 3000 ml/min for the occlusive pump. Thus, at dP=300 mmHg the user could increase the pump speed by 5 RPM to get the same flow as expected with the standard occlusive pump.

It is desirable to form the tubing 513 placed in the pump raceway of the pump loop described in FIG. 5a using a pump tubing with at least one longitudinal portion of its wall thin, the thickness of said thin wall being at least 1/10 or less that of the internal diameter of said tubing as described in my allowed application U.S. Ser. No. 07/669,641 filed Mar. 14, 1991 entitled "Innovative Pumping System For Peristaltic Pumps". The thin wall tube provides several clinical advantages. For example, as the inlet pressure to the pump is decreased, the tube starts to collapse thereby decreasing pump flow without producing excess negative inlet pressure. It would also be advantageous to extrude the pump tubing from polyurethane, preferably a polyether-polyurethane with a nominal shore hardness between 70A and 80A, as described in the aforementioned allowed application U.S. Ser. No. 07/669,641. This material has been shown to have extended pumping life and reduced spallation (the degradation of material by friction). Thus, the combination of the pressure relief valve placed across a pump tubing made of thin wall polyurethane forming a pumping loop, as for example, shown in FIG. 5a, can pump blood without producing excess inlet or outlet pressure for wider range of flow changes.

Figure 8:
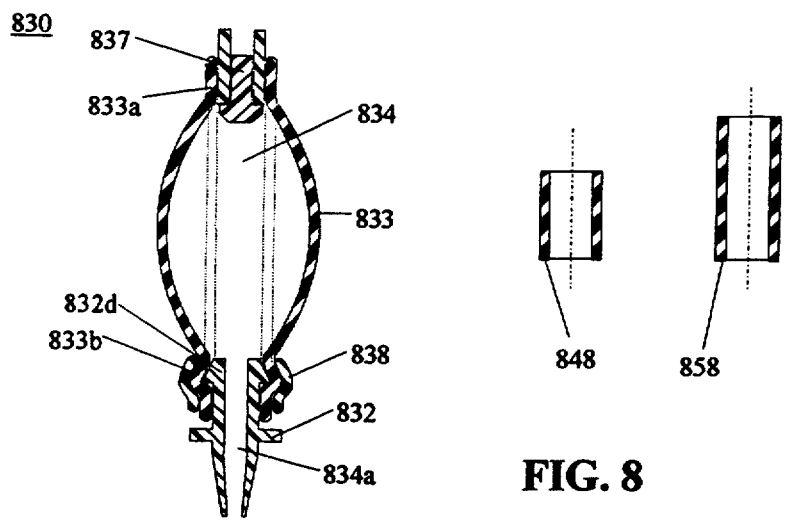
FIG. 8 is a sectional view of a preferred embodiment of a pressure regulator for valve 441 illustrated in FIGS. 5(a) and 5(d) utilizing an elastic cylindrical balloon, sealed to a check valve with a luer connection.

FIG. 8 illustrates a sectional view of another preferred embodiment of a pressure regulator designed for use with a pressure relief valve, consisting of an elastic cylindrical balloon 833 closed at one end with valve 837 and sealed to connector 832 by compression fitting 838. Connector 832, which can be for example a male Luer fitting, is configured to connect directly to port 232d of the pressure relief valve shown in FIG. 2. Check valve 837 permits pressurization of chamber 834, formed by balloon 833, connector 832, and check valve 837. The pressure in chamber 834 is transmitted through opening 834a to, for example, interluminal chamber 234 in FIG. 2. The balloon provides a steady pressure over a range of volumes that is greater than the volume change required to open and close the pressure relief valve. A cylindrical balloon has at least 4 advantages over a spherical balloon: 1) it has low manufacturing costs and higher accuracy because it can be formed by extrusion rather than molding or dipping as is the case with a spherical balloon, 2) it can be made to have an internal diameter that would accept a standard check valve, 3) its inflated state can be easily detected by a shape and size change rather than only size change for a spherical balloon, and 4) the pressure-volume relationship of a cylindrical balloon, determined by its elastic properties and physical dimensions (see co-pending application U.S. Ser. No. 876,627) can be adjusted by the user by adjusting its length. The pressure required to inflate a cylindrical balloon is a function of its internal diameter. For short balloons with a ratio of ID/length<10, the length also affects the inflating pressure. For such balloons an effective diameter can approximate the diameter to be used in the relationship between diameter and inflating pressure. Since the effective diameter for a short cylinder can be approximated by (Length×Diameter)/(Length+Diameter), then the inflating pressure for any specific cylindrical balloon can be adjusted by adjusting the length of the balloon that is allowed to expand. To that end, cylindrical sleeve 838 placed over balloon 833 limits the balloon expansion which results in a smaller balloon, a smaller effective diameter and therefore a higher inflating pressure. Sleeve 838 can also provide mechanical support to prevent the elastic cylinder from disconnecting at 833b from connector 832. Sleeve 838 can be replaced by other sleeves of different lengths, as for example sleeves 848 or 858, to yield different pressures, each of said sleeves can be marked appropriately, as for example color coded and/or numerically, to indicate the inflation volume required and/or the pressure it provides. It is also possible to provide different pressure vs. volume characteristics by having the sleeves made of an elastic material, the combination of the balloon and sleeve adapted to give desired results. Valve 837 can, for example, be a check valve (Model No. 810ACS made by Halkey Medical of St. Petersburg, Fla. 33702-1098) whose open end accepts the Luer fitting of a syringe and is designed to fill, hold and release controlled amounts of fluids on demand. Alternatively, valve 837 can be replaced with a fitting that accepts a standard 3 port stopcock with one port of the stopcock attached to the elastic sleeve, another port allowing changes in the sleeve volume, and the third connected to a conduit leading to a pressure transducer. This arrangement allows precise measurements of the controlling pressures. It should be understood by those skilled in the art that it would be advantageous if all connections required to be made by the user are formed with a standard Luer-lock fitting. It should be understood that a pressure regulator like that illustrated in FIG. 8 can be attached directly to the housing of the pressure relief valve as shown in FIGS. 5a–d.

Figure 9:
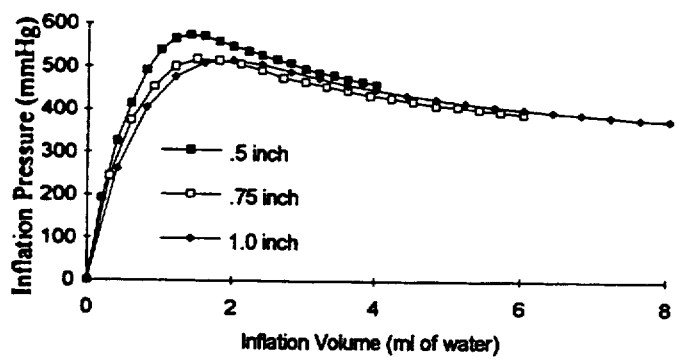
FIG. 9 illustrates the relationship between pressure and volume for a typical elastic sleeve, such as that illustrated in FIG. 8, said relationship being useful for adjusting control pressure for a pressure relief valve.

FIG. 9 illustrates the relationship between pressure and volume for different lengths of cylindrical elastic sleeves, said relationship being useful for adjusting the control pressure for a pressure relief valve. The sleeves were formed of gum rubber material with no fillers or plasticizers, cured by conventional sulfur cure system and incorporating phenolic antioxidants. The data indicates that a pressure range can be had with one sleeve by adjusting the volume and/or the length used for inflating said sleeve. For example, the data shown in FIG. 9 was collected for sleeves with an internal diameter of 0.25", a wall thickness of 0.025" and cut to lengths of 0.5 (dark squares), 0.75 (white squares) and 1.0" (diamond). Regulating pressure between 300 to 450 mmHg depending on its inflation and initial length can be obtained, indicating that the degree of inflation and/or length can be used to adjust the regulated pressure.

Figure 10:
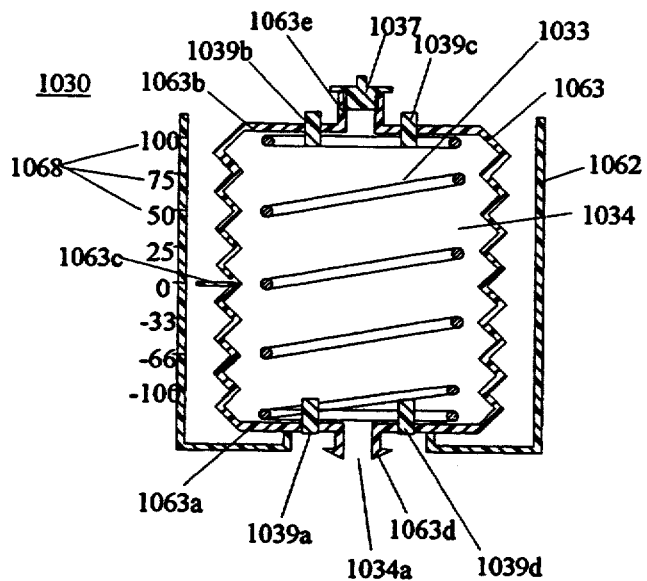
FIG. 10 is a sectional view of another preferred embodiment of a regulator incorporating a pressure indicator for controlling either negative or positive pressure applied to the pressure relief valve, utilizing a spring in a sealed flexible polymeric envelope.

FIG. 10 is a sectional view of another preferred embodiment of a pressure regulator with spring 1033 providing an elastic force. The spring is housed in, and attached to a sealed, flexible polymeric envelope 1063 forming chamber 1034. The connections are made at 1063a with 1039a and 1039d and at 1063b with 1039b and 1039c. The combination of the spring for elasticity and the envelope for sealing can provide adjustments for either control of pressure by expanding the spring, or of suction by compressing the spring via the addition or subtraction of volume into chamber 1034 respectively. This volume may be altered via check valve 1037 sealed in port 1063e. The controlled pressure is conducted through orifice 1034a, an interconnecting tubing (not shown) to, for example, port 232d of valve 531 shown in FIG. 2 and thereby to chamber 234, to impart selected negative or positive pressure upon section 53a of valve 531. The pressure generated by spring 1033 is very dependent on the degree of compression of the spring and therefore on the volume within chamber 1034. This can be used to the user's advantage by providing scale 1068 and pointer 1063c, the combination of which indicate the degree of negative or positive pressure applied on section 53a. Pressure scale 1068 can be expressed as a % of maximum negative or positive pressure possible, in mmHg or alternatively in centimeters of water.

The ratio of the volume 1034 of regulator 1030 relative to the volume change due to section 53a opening or closing can also be used to provide a variable pressure regulator. If the said change in volume of 53a is large compared to volume 1034 then as valve 531 opens, volume 1034 must increase thereby expanding spring 1033 and generating greater pressure on thin wall section 53a. If the change in said volume 53a is very small compared to the volume 1034 then there will be no significant change in 1034 as the valve opens or closes and the pressure applied to 53a would be essentially unchanged. The type of pressure regulation, steady or variable is determined by the user who can, as described for the aforementioned suction regulator, add another volume between pressure controller 1030 and controlled valve 531. It should be obvious that there are many other means for pressurizing pressure relief valves. For example, a pressure indicating means (e.g., gauge, pressure transducer) with or without a compliance chamber can be used in combination with an inflating means, as for example a syringe, to perform the same function as described for the elastic sleeve in FIG. 8.

Figure 11A:
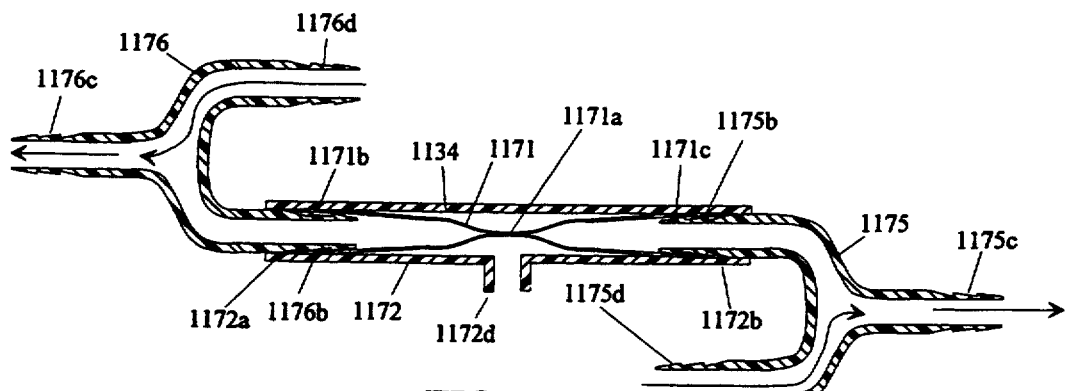
FIG. 11a illustrates a pressure relief valve utilizing the combination of a thin wall tubing a housing and Y-connectors for the valve assembly.
Figure 11B:
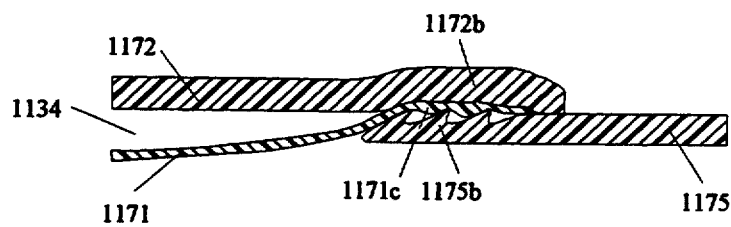
Figure 19:
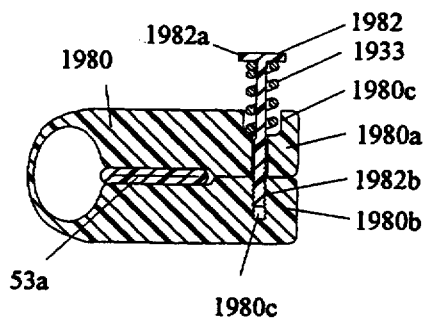
FIG. 19 illustrates a cross sectional view of a pressure relief valve with pressure regulation provided with an adjustable spring loaded clamp.

FIG. 11a illustrates a cross sectional view of a pressure relief valve utilizing 'Y-connectors', thin wall tubing and an elastic housing. Thin wall tube 1171 with one end affixed to Y-connector 1176 at 1176b and the other end affixed to Y-connector 1175 at 1175b, forms a smooth blood path. End 1175c and end 1175d of said Y-connector 1175 may be connected to the inlet of pump tubing 513a and inlet tube 34 respectively as shown in FIGS. 19 and 5a. End 1176c and end 1176d of said Y-connector 1176 may be connected to outlet tube 45 and to outlet of pump tube 513b respectively. The Y-connectors used can be, for example, standard perfusion tubing connectors supplied by Texas Medical Products of Houston Tex. Housing 1172 seals thin wall tube 1171 by forming a tight fit over 1171b onto 1176b at end 1172a and a tight fit over 1171c onto 1176b at end 1172b, as better illustrated in FIG. 11b, to form chamber 1134 whose pressure, positive or negative, can be adjusted as described previously. Thin wall tube 1171 can be made of a transparent thermoplastic, as for example polyurethane or polyvinyl chloride, as described previously, and its section 1171a serving as the pressure relief section can be formed as described with respect to FIGS. 3, 4 and 6. The advantages of this design are that the valve assembly requires no additional connectors, because it makes use of the already present Y-connectors that are used in the cardiopulmonary bypass circuit. These Y-connectors, for example as illustrated in FIG. 5a be placed such that connector 1176 replaces 3-way connector 515, connector 1175 replaces 3-way connector 514, and the pressure relief valve described herein replaces valve 441 shown in FIG. 5a, said replacements providing the same function as that described with respect to FIGS. 5a–d.

Figure 12:
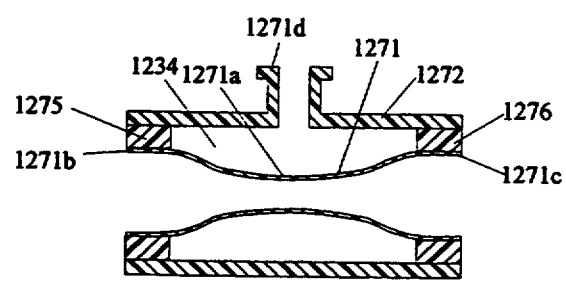
FIG. 12 illustrates an embodiment of a pressure relief valve that utilizes a thin wall sleeve attached to the housing by way of spacers.

FIG. 12 illustrates a cross sectional view of another preferred embodiment of a pressure relief valve. Thin wall tube 1271 has its ends 1271b and 1271c affixed and sealed to the inside diameter of thicker supporting sleeves 1275 and 1276 respectively. The outside diameter of supporting sleeves 1275 and 1276 are sealed to the inside diameter at each end of housing 1272 thereby forming interluminal space 1234 that can be pressurized as described, for example, with respect to FIG. 2. Midsection 1271a is processed to form a flat section such that it forms a smooth blood path and allows easy closure of opposite walls, or may be formed as described with respect to FIGS. 3, 4, and 6. The ID of the thin walled tube is made to accept standard perfusion connectors, as for example ¼" and ⅜" connectors (Baxter/Bentley Lab, Irvine Calif.) thereby allowing the user to easily incorporate said valve anywhere in the extracorporeal circuit as shown for example in FIG. 1. Thin walled tube 1271 can for example be made of polyvinyl chloride, polyurethane or other thermoplastic material used to extrude tubing for use in roller pumps. The sleeves and housing can be made of similar material to simplify the required seals between the sleeve, thin walled tubing and housing. The housing provides strength to support the interluminal pressure, and provides sufficient elasticity for the user to be able to insert said standard perfusion connectors into the thin walled tubing/sleeve/housing combination. The seals can be formed for example by solvent bonding or heat.

Figure 13:
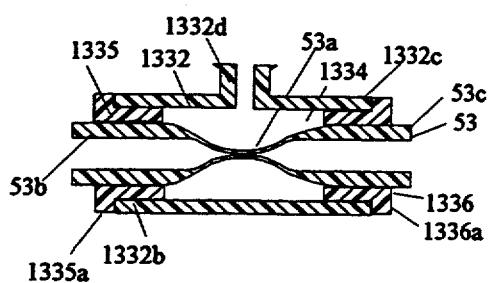
FIG. 13 illustrates an alternate embodiment forming a first pressure chamber for a pressure relief valve utilizing spacer sleeves to seal between housing and unitary tubing.

FIG. 13 illustrates a design utilizing end cap spacers 1335 and 1336 serving to secure and seal housing 1332 and unitary tubing 53. Said parts form enclosed interluminal chamber 1334 between housing ends 1332b and 1332c and the ends of the outer diameter of tube 53 at 53b and 53c. An example of the latter is part number 147ACC from Halkey-Roberts (St. Petersburg Fla. 33716) which also has a skirt shown as 1335a and 1336a for spacer 1335 and 1336 respectively. The outlet spacer may have a smaller inside diameter with thicker walls so as to constrict the outlet of the blood path, to thereby reduce fluttering as described with respect to FIG. 2.

FIG. 14 illustrates a cross section of a pressure relief valve whereby the diameter of thin section 53a has been increased to form a pressure relief valve with a wider diameter at least in one aspect of the thin wall section. The diameter should reduce the blood velocity and thereby reduce fluttering as described in reference to FIG. 2. Also illustrated is an alternate housing embodiment for thin walled region 53a utilizing a clear thermoplastic cylindrical housing sleeve 1432 made, for example, of the same material as unitary tube 53. Sleeve 1432 is heat sealed to unitary tubing 53 at 53b and 53c and to pressure control line 1423 at 1423a, said seals hermetically enclosing thin walled section 53a and forming space 1434. This design has the advantage that during assembly of the device, it is easier to insert tube 53 into large cylindrical housing 1432 after which the seals are formed rather than through the tight seals shown, for example, in FIG. 2. This design, which lends itself to inexpensive mass automated production, is also suited for pressure relief valves made of thin wall tubing as described with reference to FIG. 12.

Figure 15:
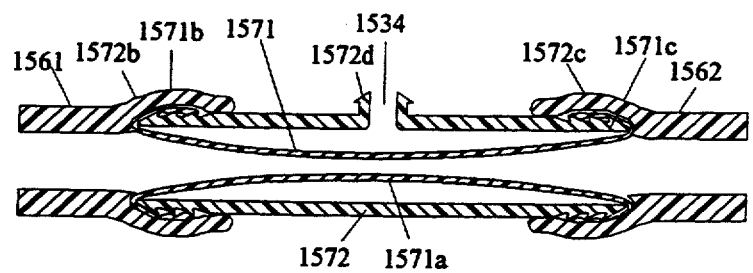
FIG. 15 illustrates a cross sectional view of a pressure relief valve constructed with a standard connector as a rigid housing forming a first pressure chamber by folding a thin wall tubing over the said connector ends.

FIG. 15 illustrates a cross sectional view of another preferred embodiment of a pressure relief valve. Thin wall tube 1571 has its ends 1571b and 1571c folded over ends 1572b and 1572c of housing 1572 respectively. The folded edges of tube 1571 are affixed and sealed to housing 1572 by standard tubing 1561 and 1562, said standard tubing positioned to entrap said thin wall tube against said connectors' ends. It may be advantageous to use protrusions such as barbed fittings on the outside diameter of housing ends to better secure the connections between said standard tubing, said thin wall tubing and said housing ends. Standard tubing 1561 and 1562 preferably consists of a length of polymeric material such as polyvinylchloride, polyurethane, C-flex or the like. Housing 1572 can for example be like a standard perfusion connector with Luer-fitting shown as 1572d (Baxter/Bentley Lab Irvine Calif.), with an ID sufficiently large to accommodate said thin wall tubing in a closed state, as explained in reference to FIG. 3. The seals made by edges 1571b and 1571c with affixed tubing 1561 and 1562 and edges 1572b and 1572c form a sealed interluminal space 1534 between the outer diameter of tubing 1571 and the inner surface of connector 1572. Connector 1572 as a standard connector comes with female luer fitting 1572d which provides communication for interluminal space 1534 and, for example, pressure regulator referred to in FIG. 8. Mid-section 1571a is processed to form a flat section such that it forms a smooth blood path and allows easy closure of opposite walls with the noted exceptions as described with respect to FIGS. 3, 4 and 6. The OD of thin walled tube is made so that when collapsed its half perimeter is slightly smaller than the ID of connector 1572. This allows equal communication of space 1534 within said valve. Standard connector 1572 allows the user to easily incorporate said valve anywhere in the extracorporeal circuit as shown for example in FIG. 1 by using standard tubing for 1561 and 1562. Thin walled tube 1571 can, for example, be made of polyvinyl chloride, polyurethane or other thermoplastic material used to extrude tubing for use in roller pumps.

Figure 16A:
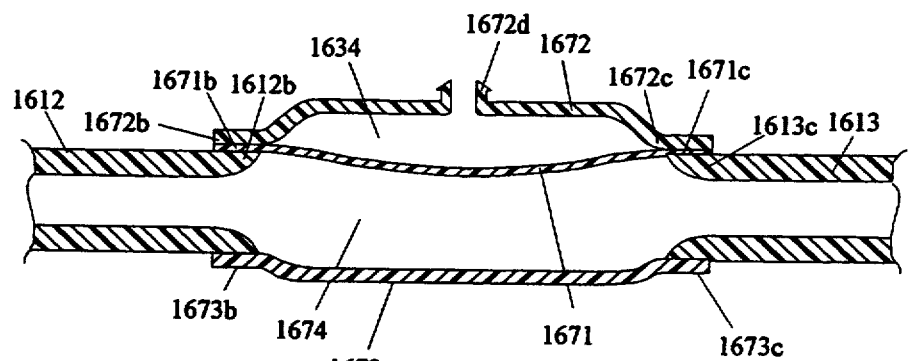
FIG. 16a illustrates a cross sectional view of a pressure relief valve constructed with a thermoplastic housing sealed to a membrane to form a first pressure chamber and a blood path.
Figure 16B:
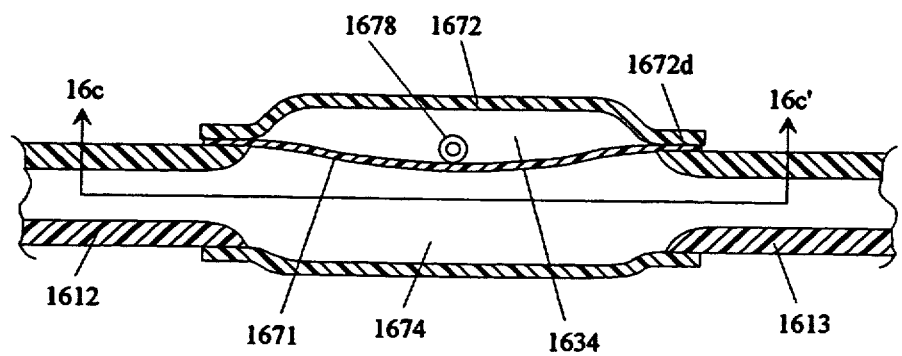
FIG. 16b illustrates a cross sectional view of a pressure relief valve constructed with a thermoplastic housing with an alternate control port construction.
Figure 16C:
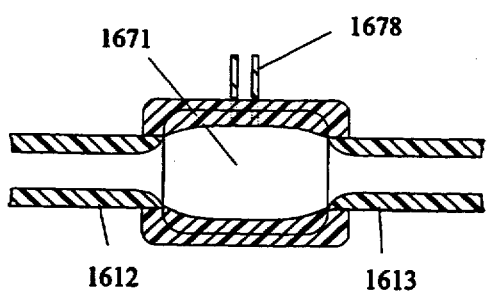
FIG. 16c illustrates cross sectional top view of the pressure relief valve shown in FIG. 16b taken along section line 16—16' with a pressure port oriented parallel to the thin wall section.

FIG. 16a illustrates a cross sectional view of a pressure relief valve constructed with 3 layers of thermoplastic membranes such as polyvinyl chloride, polyurethane or other blood compatible material that bond securely by methods such as solvent bonding, heat, RF welding or the like. As depicted, layer 1672 is sealed to thin wall membrane 1671 forming first pressure chamber 1634, and layer 1673 and thin wall membrane 1671 forms a blood path 1674 that provides communication between inlet tube 1612 and outlet tube 1613. At the inlet, tube 1612 and membrane 1671 are sealed along their perimeter between layer 1672 and 1673 sealed at 1612b, 1671b, 1672b and 1673b respectively. At the outlet, tube 1612 and membrane 1671 are sealed along their perimeter at 1612c, 1671c, 1672c and 1673c respectively. Port 1672d formed within layer 1672 provides communication between first pressure chamber 1634 and a pressure transducer means similar to that for the pressure relief valve described in FIG. 2. Port 1672d can be formed as part of layer 1672 as shown in FIG. 16a, or attached to said layer by aforementioned standard means. Alternatively, the communication port 1672d can be formed along the sealing perimeter so it is oriented parallel to thin layer 1671 as shown in FIGS. 16b and 16c, thus providing the advantage of such an orientation as described in reference to FIG. 6. Though the 3 layer design results in a valve with physical discontinuities along the seal between the thin and thick wall layers, these areas of stagnation are not prohibitive for short term use such as cardiopulmonary bypass. The advantage of the 3-layer design is that it is very adaptable to mass production. It should be understood that as explained with respect to FIGS. 5–7, it is of great clinical advantage to have at least layer 1673 transparent to allow a clear view of the open state of said valve and layer 1672 opaque white.

Figure 17A:
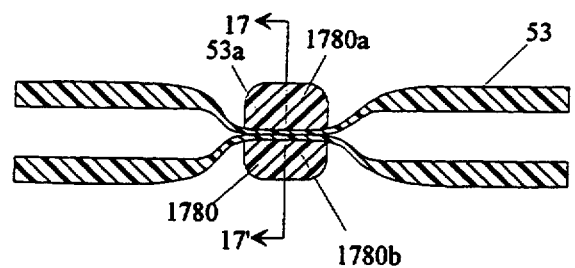
FIG. 17a illustrates a cross sectional view of a pressure relief valve with pressure regulation provided by an elastic clamp.

FIG. 17a illustrates a cross sectional view of a pressure relief valve composed of a unitary tube 53 having thin wall section 53a that is maintained closed by an elastic loaded clamp 1780. As shown, in FIG. 17b, which is a sectional view along line 17—17' of the pressure relief valve shown in FIG. 17a, thin wall section 53a is squeezed shut between section 1780a and 1780b of clamp 1780. The force of closure is provided by the resiliency of ring 1780c of clamp 1780 and/or by elastic band 1733. The force of closure must be equal to or greater than the force required to overcome the elasticity of section 53a plus the separating force due to any pressure difference across the thin wall section 53a. When the pressure within tube 53 increases to generate a force greater than said elastic force, section 53a opens, opening pressure relief valve in a similar manner as explained with respect to FIGS. 2–4. The pressure at which the valve opens can be adjusted by the physical parameters of band 1733 or ring 1780c. For example, increasing the width, decreasing the diameter or increasing the thickness of band 1733 or ring 1780c would increase the pressure at which the valve would open.

Figure 17B:
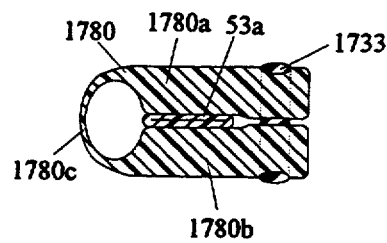
Figure 18A:
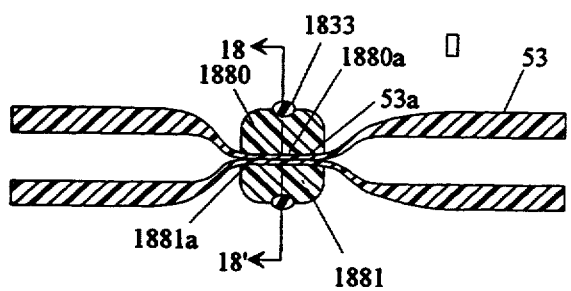
FIG. 18a illustrates a cross sectional view of a pressure relief valve with pressure regulation provided with another form of an elastic clamp.
Figure 18B:
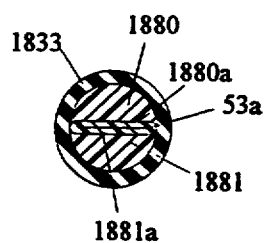

FIG. 18a illustrates a cross sectional view of a pressure relief valve with pressure regulation provided with another form of a clamp similar to the clamp described in FIGS. 17a and 17b. Here, the thin wall section 53a is sandwiched between two members, 1880 and 1881, each of said members having a flat surface 1880a and 1881a respectively said flat surface contacting thin wall section 53a as shown in FIGS. 18a and 18b, the latter being a sectional view along line 18—18′ of the pressure relief valve shown in FIG. 18a. Members 1880 and 1881 are forced towards each other to squeeze section 53a closed by the force of elastic band 1833. Assuming that the walls of section 53a are free to move, the pressure relief valve opens when the pressure within tube 53a is sufficient to overcome the force of elastic band 1833.

FIG. 19 illustrates a cross sectional view of a pressure relief valve similar to that shown in FIGS. 17a and 17b except that the closing force provided by the elastic band has been replaced by an adjustable spring force. As shown, thin wall section 53a is squeezed shut between section 1980a and 1980b of clamp 1980. The force of closure is provided by spring 1933, said spring being supported at one end by rotational member 1982 and at its other end by slot 1980c in clamp portion 1980a. The closure force provided by the spring can be adjusted by rotational member 1982, said member having head 1982a used for rotation at one end and a thread at its other end 1982b, said threaded end engaging mating thread 1980c in clamping portion 1980. By rotating member 1982, spring 1933 can be squeezed or released thereby providing an adjustable force. Appropriate selection of spring 1933 allows various permutations of controls. For example, using a long spring with a low spring constant (Force=Spring constant*Compressed distance) would require greater compression than a short spring with a larger spring constant. The longer spring would result in a fairly constant opening force because the distance required to open the valve (separate walls of section 53a) is insignificant compared to the overall distance the spring is compressed. Similarly, the shorter spring would require an increased opening force because the distance required to open the valve is significant compared to the overall distance the spring is compressed. It should be obvious to those skilled in the art that other permutations of spring length, spring force, spring shape or the shape of the spring wire can easily be designed. It should also be obvious that washers and/or spacers can be placed between advancing and rotational parts, as for example between said spring 1933 and said rotational member 1982.

Figure 20A:
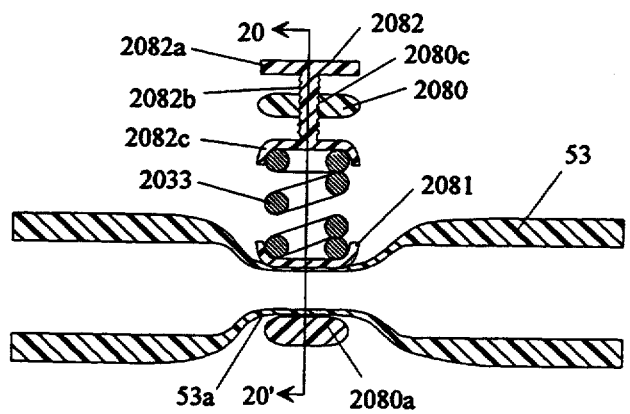
FIG. 20a illustrates a cross sectional view of a pressure relief valve with pressure regulation provided with another type of an adjustable spring loaded clamp.
Figure 20B:
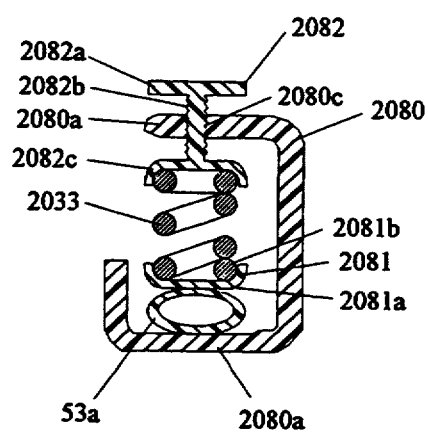

FIGS. 20a and 20b illustrate a cross sectional view of another pressure relief valve similar to that shown in FIG. 19 also utilizing an adjustable spring force to close thin wall section 53a with the spring force directly over said section 53a. As shown, section 53a is placed and is supported within C frame 2080. Section 53a is squeezed on one of its sides by the lower section 2080a of said C frame and on its other side by upper clamping means 2081. Rotating member 2082 engages one side of spring 2033 forcing it against said upper clamping means 2081. The magnitude of said force depends on the characteristics of the spring and the degree of spring compression, said compression being adjustable by rotating member 2082 thereby moving said member in relation to said C frame by way of thread 2080c that mates a corresponding thread 2082c of rotating member 2082. Functionally, the spring replaces the pressure within first pressure chamber described for pressure relief valve in FIG. 2, where higher compression requires increased blood pressure to open thin wall section 53a.

The arrangement shown in FIGS. 20a and 20b could also be used to control negative pressure as described with respect to FIG. 22. For suction control, spring 2033 would be affixed to rotating member at 2082c and to upper clamping means at 2081b. In addition, the outer walls of section 53a that are parallel to, and are squeezed by upper clamping means 2081 at 2081a and section 2080a of said C frame, would be attached along their plane of contact to said section of C frame and upper clamping means. By anchoring said thin section to the clamp 2080 and c-clamp means 2081 by adhesive or heat seal, and by having rotational means 2082 expand spring 2033, section 53a would be normally open, closing when the blood pressure drops below atmospheric pressure to a level sufficient to overcome the resilience of spring 2033 that otherwise maintains said section open. The negative pressure at which the valve closes can be adjusted by said rotational means expanding said spring by moving further away from said section 2080a of said C-frame. To assure visualization of the open/close state of the valve as explained with regards to FIG. 7a, it is desirable to have at least one side of the c-clamp transparent.

Figure 21A:
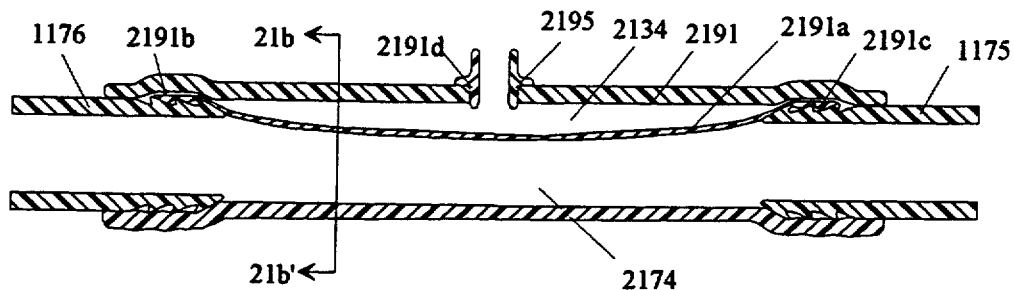
FIG. 21a illustrates another embodiment of a pressure relief valve wherein an extruded tube with a thin wall separating the blood flowpath and pressure regulating chamber is used to form the pressure sensitive device.
Figure 21B:
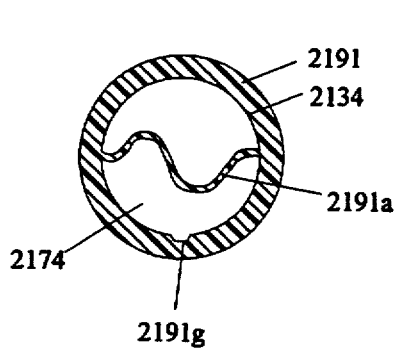
FIG. 21b is a cross sectional view of a pressure relief valve as shown in FIG. 21a taken along line 21b—21b.

FIG. 21a illustrates a pressure relief valve utilizing the combination of a tube, extruded with a thin wall separating two sides of said tube, and perfusion connectors for the valve assembly and blood flow. Tube 2191 with one end affixed to perfusion connector 1176 and the other end affixed to perfusion connector 1175 forms a smooth blood path 2174. Thin wall section 2191A is extruded as part of tubing 2191 as illustrated in FIG. 21b. Perfusion connectors 1176 and 1175 seal section 2191A to the inside diameter of tube 2191 at sections 2191B and 2191C respectively, creating interluminal space 2134. Interluminal space 2134 may have positive or negative pressure which may be adjusted and regulated as described previously. An additional connector 2195 must be affixed to tube 2191 at section 2191d in order to allow connection to a pressure regulating device described previously. The advantages of this design are that the valve is extruded as a single piece of tubing, and the valve assembly makes use of the already present perfusion connectors that are used in the cardiopulmonary bypass circuit. These perfusion connectors can for example be placed such that connector 1176 can replace 3-way connector 515, connector 1175 can replace 3-way connector 514, and the pressure relief valve described herein can replace valve 441 shown in FIG. 5a, said replacements providing the same function as that described with respect to FIG. 5. The arch or length of thin wall 2191A may be altered by altering the perimeter of the external curvature to provide a valve with a complete or partial closure. The thickness of thin wall 2191a may be adjusted to force the formation of one or two bleed channels at the point the thin wall joins the tube wall. Providing a thicker wall adjacent the tube wall will create a bleed channel adjacent the thick wall. Bleed channel 2191g may also be extruded into the thick wall section 2191 at the time the section is extruded. Shortening the overall length of thin wall 2191A will enable partial closure for modulating, but not stopping, flow through this valve configuration.

Figure 21C:
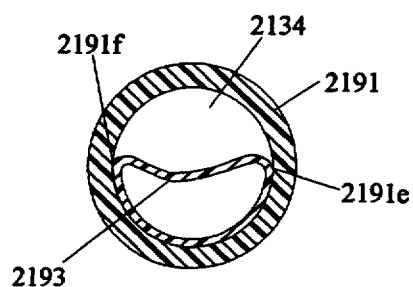
FIG. 21c illustrates another embodiment of a pressure relief valve, wherein a coextruded tube with a thin wall is formed inside the tube to separate the blood and pressure regulating chambers.

FIG. 21c illustrates a cross sectional view of another embodiment for a pressure relief valve as shown in FIG.

21b except that a coextruded tube with a thin wall inside layer separating the blood and pressure regulating is utilized. As shown, tube 2191 with a heavier wall is coextruded with a thin wall tube 2193, after which the two layers are peeled apart to form first pressure chamber 2134 similar to that shown in FIG. 21a as coextruded inside said tube. Tube 2193 is sealed to tube 2191 from section 2191E to 2191F. Either of the embodiments illustrated in FIG. 21b and FIG. 21c may be further altered in a post extrusion procedure, to alter the configuration of the thin wall. For example, the resistance of wall 2191a to completely close can be significantly reduced by postextrusion by forcing a heated rod through the extruded section, or by flattening the entire assembly at the mid section thereof.

FIG. 22 shows pressure relief valve 281 placed at the inlet to roller pump 9. As illustrated, the pump used for suction and the pressure relief valve is used to limit the negative pressure applied to the blood at the inlet to said valve. It also provides easy means to set occlusion of the pump. Thus, the pressure within first chamber is set by, for example, aforementioned negative pressure regulator 1030 described in FIG. 10, such that pressure relief valve, for example as described in FIG. 2, is normally open as long as the blood pressure at the outlet of valve 281 remains above pressure in said first chamber. To set the occlusion of pump 9, the pressure in first pressure chamber 2234 is set to a desired negative level (e.g., −50 mmHg), the inlet to valve 281 is clamped off, the pump is set to a desirable speed (e.g., 50 RPM) and the occlusion of pump 9 is adjusted with adjuster 510c until flow through the valve just occurs as described in reference to FIGS. 7a and 7b. At the appropriate occlusion, the forward flow provided by the pump is equal to the back flow through nonocclusive section 2228. It should be noted that the negative pressure can also be set in a less accurate way by removing a known volume from chamber 2234 thereby reducing its pressure and maintaining the valve open until the blood pressure exceeds the negative pressure required to close said valve. As section 28a collapses, the negative pressure in chamber 2234 changes as a function of the ratio of the volume in chamber 2234 to the volume change caused by said collapse as explained with respect to FIG. 10. It is noted that when a pressure relief valve is created for suction control, the housing should be sufficiently rigid to withstand any deformation that could affect said negative pressure.

Figure 23:
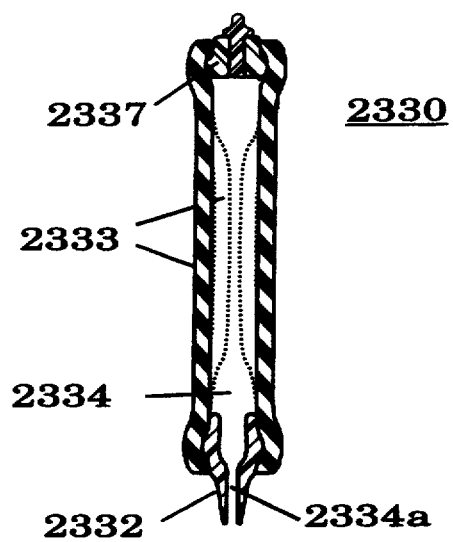
FIG. 23 is a sectional view of a preferred embodiment of a negative pressure regulator utilizing an elastic cylindrical balloon, sealed to a luer connection.
Figure 24:
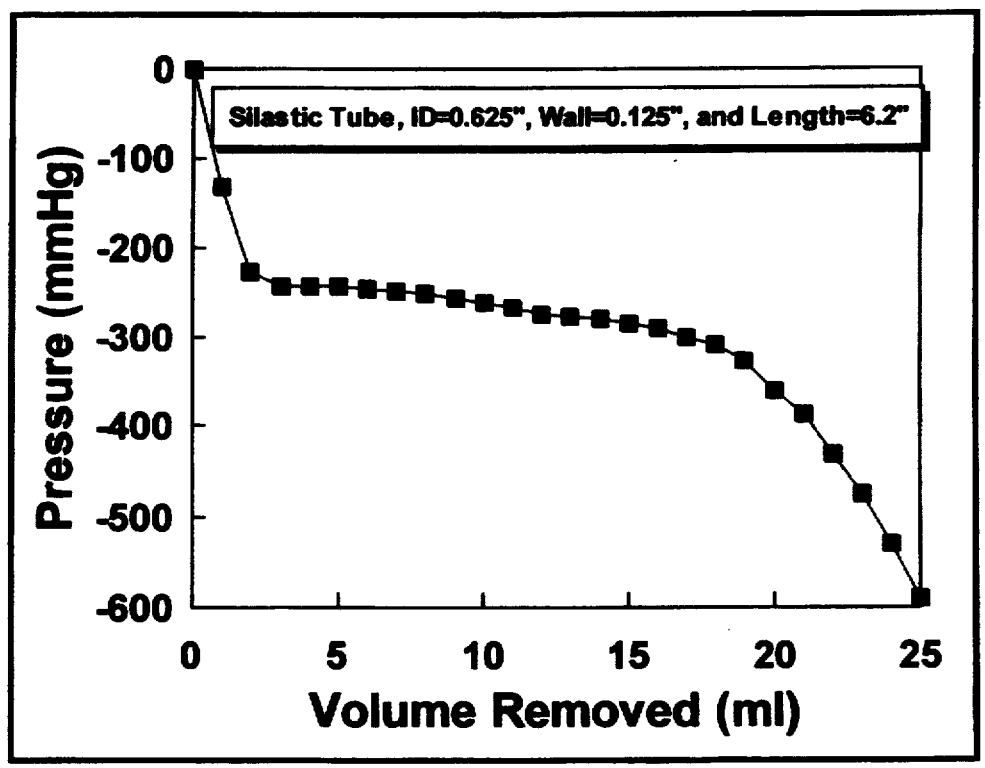
FIG. 24 illustrates the relationship between pressure and volume for a typical elastic sleeve, such as that illustrated in FIG. 23, said relationship being useful for adjusting negative control pressure for a pressure relief valve.

FIG. 23 illustrates a sectional view of another preferred embodiment of a regulator 2030 designed for use with a pressure relief valve that will generate negative pressure. Regulator 2330 includes an elastic cylindrical balloon 2333 closed at one end with check valve 2337 and sealed to connector 2332 by a compression fitting. Connector 2332, which can be for example a male Luer fitting, is configured to connect directly to port 2332d of the pressure relief valve shown in FIG. 22. Check valve 2337 permits evacuation of and maintenance of generated negative pressure within chamber 2334, said chamber formed by sleeve 2333, connector 2332, and check valve 2337. The pressure in chamber 2334 is transmitted through opening 2334a to, for example, interluminal chamber 2234 in FIG. 22. A typical relationship between the volume and internal pressure of a regulator made from a 6.2" long silastic tube ⅜" ID, and ⅛" wall is shown in FIG. 24. As can be seen, the negative pressure generated by said sleeve provides either a variable or constant pressure curve depending where along the curve one chooses to operate. When operating in the mid range, a fairly constant pressure is obtained independent of the volume. For this range, the collapsed state of the sleeve, as indicated by the dashed lines in FIG. 23, can be used to indicate that negative pressure is being applied to chamber 2234 of valve 281. It should be obvious that different curves can be generated depending on the material and the length and ratio of ID to wall thickness, as explained in FIG. 8. It should also be understood by those skilled in the art that it would be advantageous if all connections required to be made by the user are formed with a standard Luer-lock fitting. It should also be understood that a pressure regulator 2330 can be attached directly to the port of the pressure relief valve 441 shown in FIG. 5.

What is claimed:

1. An improved pump loop for use with a roller pump for extracorporeal circulation; said loop comprising:
   (a) a first tubing segment for insertion in a roller pump for pumping extracorporeal fluids there through, said tubing having a pump inlet and a pump outlet;
   (b) a shunt tubing for fluid connection of said pump outlet to said pump inlet;
   (c) a pressure relief valve for closing said shunt tubing below a predetermined pressure.

2. An improved pump loop as claimed in claim 1 wherein said pressure relief valve further includes a thin wall tubing portion formed in said shunt tubing between said pump outlet and said pump inlet.

3. A device as claimed in claim 2 wherein said pressure relief valve includes a resiliently biased tubing clamp which closes and clamps said thin wall portion below a predetermined pump outlet pressure.

4. A device as claimed in claim 3 wherein said elastic member has a predetermined cross sectional area and preload while said clamp geometry defines a predetermined elongation of said elastic member in response to a predetermined pump outlet pressure.

5. An improved pump loop as claimed in claim 4 wherein said pressure relief valve further includes a thin wall tubing and a housing which surrounds said thin wall tubing to define a first pressure chamber between said housing and said thin wall tubing.

6. An improved pump loop as claimed in claim 5 which further includes means for pressurizing said first pressure chamber to a predetermined pressure.

7. An improved pump loop as claimed in claim 2 or 3 wherein said pressure relief valve further includes a housing which surrounds said thin wall to define a first pressure chamber between said housing and said thin wall tubing.

8. An improved pump loop as claimed in claim 7 which further includes means for pressurizing said first pressure chamber to a predetermined pressure.

9. An improved pump loop as claimed in claim 8 wherein said means for pressurizing further includes a pressurized elastic sleeve.

10. An improved pump loop as claimed in claim 8 wherein said means for pressurizing further includes a spring loaded pressure regulator.

11. An improved pump loop as claimed in claim 8 wherein said means for pressurizing further includes a pressure gauge and means for manually pressurizing said pressure chamber.

12. An improved pump loop as claimed in claim 2 or 3 wherein said housing is elliptical with means to snugly engage said shunt tubing on each side of said thin wall.

13. An improved pump loop as claimed in claim 1 wherein said pressure relief valve further includes a thin wall section mounted between said pump outlet and said pump inlet.

14. An improved pump loop as claimed in claim 2 or 3 wherein said thin wall is formed with flattened side walls which occlude said shunt below said predetermined pressure.

15. An improved pump loop for use with a roller pump as claimed in claim 1 wherein said loop further includes means for setting roller pump occlusion.

16. An improved pump loop for use with a roller pump as claimed in claim 15 in which said means for setting roller pump occlusion further includes means for clamping the pump outlet of said first tubing segment.

17. A device for use with a roller pump in extracorporeal circulation; said device comprising:
 (a) a first tubing segment for insertion in a roller pump for pumping extracorporeal fluids there through, said tubing having pump inlet and pump outlet;
 (b) a shunt tubing for fluid connection of said pump outlet to said pump inlet;
 (c) a pressure relief valve for closing said shunt tubing below a predetermined pressure;
 (d) first means for indicating fluid flow from said pump outlet to said pump inlet through said shunt tubing.

18. A device as claimed in claim 17 wherein said first means is provided by forming said shunt tubing from a transparent material which allows a visual observation of closure of said pressure relief valve.

19. A device as claimed in claim 17 which further includes a transparent housing which surrounds a portion of said shunt tubing to form said pressure relief valve, said chamber and said portion being formed of transparent material to allow a visual observation of closure of said pressure relief valve, by a change in the optical characteristics of said shunt tubing.

20. A device as claimed in claim 19 wherein said portion of shunt tubing forms flattened walls when pressured to define a plane oriented from 30° to 60° from a horizontal plane.

21. A device as claimed in claim 20 wherein said thin wall portion defines at least one bleed channel between said flattened walls.

22. A device as claimed in claim 19 wherein the chamber formed between is pressurized to a predetermined value to define said pressure relief value.

23. A device as claimed in claim 22 wherein said first pressure chamber is filled with incompressible fluid.

24. A device as claimed in claim 22 wherein said first pressure chamber is filled with compressible fluid.

25. A device as claimed in claim 24 wherein said tubing clamp is formed with first and second clamping jaws secured on a first side by a resilient hinge and on the second side by an elastic member.

26. An improved pump loop for use with a roller pump in extracorporeal circulation, said loop comprising:
 (a) a first tubing segment for insertion in a roller pump for pumping extracorporeal fluids therethrough, said tubing having a first 3-way connector at the pump outlet and a second 3-way connector at the pump inlet;
 (b) a pressure relief valve with an inlet and an outlet, said inlet connected to said first 3-way connector and said outlet connected to said second 3-way connector, said pressure relief valve formed to open in response to a pump outlet pressure above a predetermined value;
 (c) shunt tubing providing extracorporeal fluid flow between said first 3-way connector, through said pressure relief valve to said second 3-way connector when said pressure relief valve is open;
 whereby said loop relieves excess pump outlet pressure by venting extracorporeal fluid from said pump outlet to said pump inlet when the pump outlet pressure exceeds a predetermined value.

27. A system for regulating pressure in an extracorporeal circuit, said system comprising:
 (a) an extracorporeal circuit for circulation of blood, said circuit having at least a plurality of blood compatible tubing members with connectors therebetween for circulation of blood therethrough, said circuit having a plurality of devices for circulating and treating blood, each device having at least a blood inlet side and a blood outlet side;
 (b) at least one shunt tubing bridging one of said devices and connecting said outlet side to said inlet side.
 (c) a pressure responsive valve normally closing said shunt tubing below a predetermined pressure;
 whereby said pressure responsive valve will open to allow blood flow through said shunt with the blood pressure in the shunt is greater than said predetermined pressure.

28. An adjustable safety device for indicating overpressure conditions in an extracorporeal circuit, said device comprising:
 (a) a first tubing segment for insertion in an extracorporeal circuit for circulating blood from a patient through a plurality of devices;
 (b) a pump means for circulating blood through said circuit and said tubing segment;
 (c) a shunt means connecting said first tubing member and a blood reservoir;
 (d) an adjustable pressure sensitive valve normally closing said shunt below a predetermined pressure;
 whereby overpressurization is indicated by a flow of blood into said blood reservoir.

29. An adjustable safety device as claimed in claim 28 wherein an air interface is provided for said reservoir, and said flow of blood is visible through said air interface.

* * * * *